(12) United States Patent
Chen et al.

(10) Patent No.: US 8,604,235 B2
(45) Date of Patent: *Dec. 10, 2013

(54) PRODUCTION OF SUBSTITUTED PHENYLENE AROMATIC DIESTERS AND COMPOSITIONS

(75) Inventors: Linfeng Chen, Missouri City, TX (US); Tak W. Leung, Houston, TX (US); Tao Tao, Houston, TX (US); Xiaodong Huang, Lake Jackson, TX (US); James X. Shu, legal representative, Houston, TX (US); Kuanqiang Gao, Pearland, TX (US)

(73) Assignee: Dow Global Technologies LLC, Midland, MI (US)

( * ) Notice: Subject to any disclaimer, the term of this patent is extended or adjusted under 35 U.S.C. 154(b) by 26 days.

This patent is subject to a terminal disclaimer.

(21) Appl. No.: 12/651,268

(22) Filed: Dec. 31, 2009

(65) Prior Publication Data

US 2010/0204506 A1   Aug. 12, 2010

Related U.S. Application Data

(60) Provisional application No. 61/141,959, filed on Dec. 31, 2008.

(51) Int. Cl.
*C07C 69/76* (2006.01)

(52) U.S. Cl.
USPC .......................................................... 560/85

(58) Field of Classification Search
None
See application file for complete search history.

(56) References Cited

U.S. PATENT DOCUMENTS

| 7,935,766 B2 * | 5/2011 | Sheard et al. | 525/323 |
| 2005/0239636 A1 * | 10/2005 | Gao et al. | 502/103 |

OTHER PUBLICATIONS

Raiford et al. (J. Amer. Chem. Soc., 1933, 55, 4288).*
English translation of Mueller et al. (Justus Liebigs Annalen der Chemie, 1965, 688, 134).*
Nakamatsu et al., Org. Biomol. Chem., 2003, 1, 2231-2234.
Adam et al., J. Org. Chem., 1984, 49, 3920-3928.
Pospisil et al., Collection Czechoslov. Chem. Commun., vol. 31, 1966, 1839-1847.
Falshaw, et al., Journal of the Chemical Society, Chemical Society, Letchworth, GB, Jan. 1, 1963, 2422-2428.
Muller et al., Liebigs Ann. Chem., vol. 688, 1965, pp. 134-149.

* cited by examiner

*Primary Examiner* — Johann R Richter
*Assistant Examiner* — Jennifer C Sawyer
(74) *Attorney, Agent, or Firm* — Whyte Hirschboeck Dudek S.C.

(57) ABSTRACT

The present disclosure provides processes for the production of substituted phenylene aromatic diesters and the resultant compositions. The processes include reacting an aromatic diol with an aromatic carboxylic acid or a derivative thereof. The aromatic diol and/or the aromatic carboxylic acid (or derivative thereof) is/are substituted. The reaction forms a substituted phenylene aromatic diester with the structure (II):

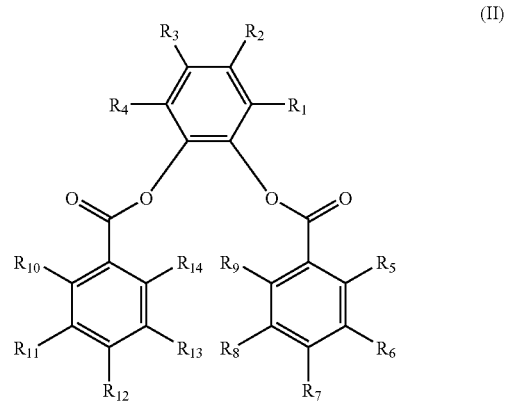

wherein $R_1$-$R_{14}$ are the same or different. At least one of $R_1$-$R_{14}$ is selected from a substituted hydrocarbyl group having 1 to 20 carbon atoms, an unsubstituted hydrocarbyl group having 1 to 20 carbon atoms, an alkoxy group having 1 to 20 carbon atoms, a heteroatom, and combinations thereof.

6 Claims, No Drawings

PRODUCTION OF SUBSTITUTED PHENYLENE AROMATIC DIESTERS AND COMPOSITIONS

PRIORITY CLAIM

This application claims priority to U.S. provisional patent application Ser. No. 61/141,959 filed on Dec. 31, 2008, the entire content of which is incorporated by reference herein.

BACKGROUND

The present disclosure relates to substituted 1,2-phenylene aromatic diesters.

A known synthesis for unsubstituted phenylene dibenzoate is esterification of catechol with benzoyl chloride in a liquid medium. Substituted phenylene dibenzoate shows promise as a component in improved catalyst systems for the production of olefin-based polymers having improved properties. Consequently, the art recognizes the need for improved processes for the production of substituted phenylene aromatic diesters and the resultant compositions.

SUMMARY

The present disclosure is directed to substituted 1,2-phenylene aromatic diesters.

In an embodiment, a process for producing a diester is provided. The process includes reacting a substituted aromatic diol with an aromatic carboxylic acid or derivative thereof under reaction conditions. The reaction forms a substituted 1,2-phenylene dibenzoate of the structure (II):

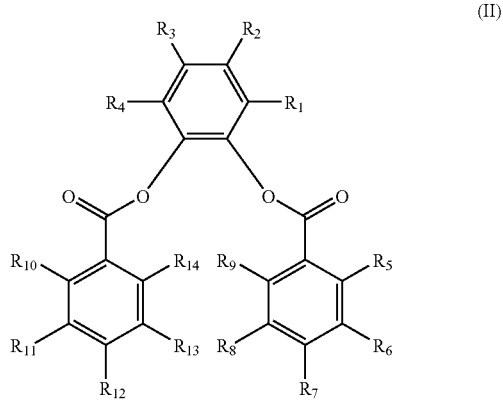

(II)

wherein $R_1$-$R_{14}$ are the same or different. At least one of $R_1$-$R_4$ is selected from an unsubstituted hydrocarbyl group having 2 to 20 carbon atoms and a substituted hydrocarbyl group having 2 to 20 carbon atoms. Each of the other R groups of $R_1$-$R_4$ is hydrogen. Each of $R_5$-$R_{14}$ is selected from hydrogen, an unsubstituted hydrocarbyl group having 1 to 20 carbon atoms, a substituted hydrocarbyl group having 1 to 20 atoms, an alkoxy group having 1 to 20 carbon atoms, a halogen, and combinations thereof.

In an embodiment, the process includes selecting a substituted catechol wherein neither $R_1$ nor $R_2$ is a methyl group when each of the other R groups of $R_1$-$R_{14}$ groups is hydrogen.

The disclosure provides another process for producing a diester. In an embodiment, a process for producing a diester includes reacting a substituted aromatic diol with a substituted aromatic acyl halide under reaction conditions. The reaction forms a substituted 1,2-phenylene dibenzoate of the structure (II) wherein $R_1$-$R_{14}$ are the same or different. At least one of $R_1$-$R_4$, at least one of $R_5$-$R_9$, and at least one of $R_{10}$-$R_{14}$ is selected from an unsubstituted hydrocarbyl group having 1 to 20 carbon atoms, a substituted hydrocarbyl group having 1 to 20 carbon atoms, an alkoxy group having 1 to 20 carbon atoms, a halogen, and combinations thereof.

The disclosure provides another process for producing a diester. In an embodiment, a process for producing a diester includes reacting an aromatic diol with a di-substituted carboxylic acid or derivative thereof under reaction conditions. The reaction forms a substituted 1,2-phenylene dibenzoate of the structure (II) wherein $R_1$-$R_{14}$ are the same or different. At least two of $R_5$-$R_9$, and at least two of $R_{10}$-$R_{14}$ are selected from an unsubstituted hydrocarbyl group having 1 to 20 carbon atoms, a substituted hydrocarbyl group having 1 to 20 carbon atoms, an alkoxy group having 1 to 20 carbon atoms, a halogen, and combinations thereof.

The disclosure provides another process for producing a diester. In an embodiment, a process for producing a diester includes reacting an aromatic diol with a first aromatic carboxylic acid or derivative thereof and a second aromatic carboxylic acid or derivative thereof under reaction conditions. The reaction forms a substituted 1,2-phenylene dibenzoate of the structure (II) wherein $R_1$-$R_{14}$ are the same or different. Each of $R_1$-$R_{14}$ is selected from hydrogen, a substituted hydrocarbyl group having 1 to 20 carbon atoms, an unsubstituted hydrocarbyl group having 1 to 20 carbon atoms, an alkoxy group having 1 to 20 carbon atoms, a halogen, and combinations thereof. At least one of $R_5$-$R_9$ is different than its respective $R_{10}$-$R_{14}$ mate.

The disclosure provides another process for producing a diester. In an embodiment, a process for producing a diester includes reacting a dihydroxynaphthalene with a carboxylic acid or derivative thereof under reaction conditions. The reaction forms a substituted 1,2-phenylene dibenzoate wherein $R_1$-$R_{14}$ are the same or different. In an embodiment, $R_2$ and $R_3$ are members of a $C_6$ aromatic ring. In a further embodiment, at least one R group of $R_1$-$R_{14}$ is not hydrogen.

The disclosure provides another process for producing a diester. In an embodiment, a process for producing a diester includes reacting an aromatic diol with a naphthoyl halide under reaction conditions. The reaction forms a substituted 1,2-phenylene dibenzoate (II) wherein any two consecutive R groups in $R_5$-$R_9$ and/or any two consecutive R groups in $R_{10}$-$R_{14}$ are members of a $C_6$ aromatic ring.

The disclosure provides a composition. In an embodiment, a substituted phenylene aromatic diester is provided having the structure (II):

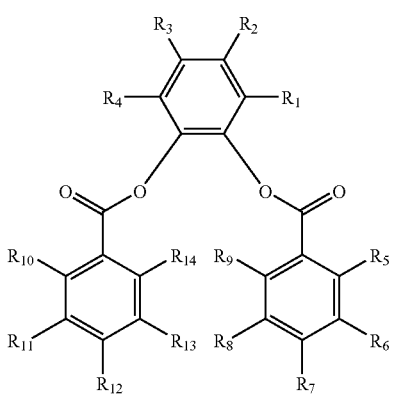

(II)

wherein $R_1$-$R_{14}$ are the same or different. $R_1$ is not an isopropyl group or a tertiary alkyl group. Each of $R_1$ and $R_3$ is selected from an unsubstituted alkyl group having 1 to 20 carbon atoms, an alkenyl group having 1 to 20 carbon atoms, a halohydrocarbyl group, a halogen, a silicon-containing hydrocarbyl group, and combinations thereof. Each of $R_2$, $R_4$, and $R_5$-$R_{14}$ is selected from hydrogen, an unsubstituted hydrocarbyl group having 1 to 20 carbon atoms, a halohydrocarbyl group, a halogen, and combinations thereof.

The present disclosure provides another composition. In an embodiment, a substituted phenylene aromatic diester of the structure (II) is provided. $R_1$-$R_{14}$ are the same or different. $R_1$ is an unsubstituted hydrocarbyl group having 1 to 20 carbon atoms. Each of $R_2$-$R_4$ is selected from hydrogen, an unsubstituted hydrocarbyl group having 1 to 20 carbon atoms, a halohydrocarbyl group, a halogen, a silicon-containing hydrocarbyl group, and combinations thereof. Each of $R_5$-$R_{14}$ is selected from an unsubstituted hydrocarbyl group having 1 to 20 carbon atoms, a halohydrocarbyl group, a halogen, a silicon-containing hydrocarbyl group, and combinations thereof.

The present disclosure provides another composition. In an embodiment, a substituted phenylene aromatic diester of the structure (II) is provided. $R_1$-$R_{14}$ are the same or different. $R_2$ is an alkyl group having 2 to 20 carbon atoms. Each other R group of $R_1$-$R_4$ is hydrogen. Each of $R_5$-$R_{14}$ is selected from hydrogen, an unsubstituted hydrocarbyl group having 1 to 20 carbon atoms, a halohydrocarbyl group, a halogen, a silicon-containing hydrocarbyl group, and combinations thereof. The R groups $R_2$, $R_7$, and $R_{12}$ are simultaneously not a t-butyl group.

The present disclosure provides another composition. In an embodiment, a substituted phenylene aromatic diester with the structure (II) is provided. $R_1$-$R_{14}$ are the same or different. Each of $R_1$, $R_3$, $R_4$ is hydrogen. $R_2$ is a hydrocarbyl group having 1 to 20 carbon atoms. At least one of $R_7$ and $R_{12}$ is a halogen. Each of $R_5$-$R_6$, $R_8$-$R_{11}$ and $R_{13}$-$R_{14}$ is selected from hydrogen, an unsubstituted hydrocarbyl group having 1 to 20 carbon atoms, a halohydrocarbyl group, a halogen, a silicon-containing hydrocarbyl group, and combinations thereof.

The disclosure provides another composition. In an embodiment, a substituted phenylene aromatic diester is provided having the structure (II). $R_1$-$R_{14}$ are the same or different. Each of $R_1$, $R_3$, $R_4$ is hydrogen. $R_2$ is a hydrocarbyl group having 1 to 20 carbon atoms. Each of $R_5$-$R_{14}$ is selected from hydrogen, an unsubstituted hydrocarbyl group having 1 to 20 carbon atoms, a halohydrocarbyl group, a halogen, a silicon-containing hydrocarbyl group, and combinations thereof. At least one of $R_5$-$R_6$, $R_8$-$R_{11}$ and $R_{13}$-$R_{14}$ is selected from a $C_1$-$C_6$ alkyl group, a halogen, and combinations thereof.

The disclosure provides another composition. In an embodiment, a substituted 1,2-phenylene aromatic diester of the structure (II) is provided. $R_1$-$R_{14}$ are the same or different. $R_1$ is not a secondary alkyl group or a tertiary alkyl group. Each of $R_1$ and $R_4$ is selected from an unsubstituted alkyl group having 1 to 20 carbon atoms, an alkenyl group having 1 to 20 carbon atoms, a halohydrocarbyl group, a halogen, a silicon-containing hydrocarbyl group, and combinations thereof. Each of $R_2$-$R_3$ and each of $R_5$-$R_{14}$ is selected from hydrogen, unsubstituted hydrocarbyl group having 1 to 20 carbon atoms, a halohydrocarbyl group, a halogen, a silicon-containing hydrocarbyl group, and combinations thereof.

Another composition is provided. In an embodiment, a substituted phenylene aromatic diester of the structure (II) is provided. $R_1$-$R_{14}$ are the same or different. Each of $R_1$-$R_{14}$ is selected from hydrogen, an unsubstituted hydrocarbyl group having 1 to 20 carbon atoms, a halohydrocarbyl group, a halogen, a silicon-containing hydrocarbyl group, and combinations thereof. At least one of $R_5$-$R_9$ is different than its respective $R_{10}$-$R_{14}$ mate.

Another composition is provided. In an embodiment, a substituted phenylene aromatic diester is provided with the structure (IV) below.

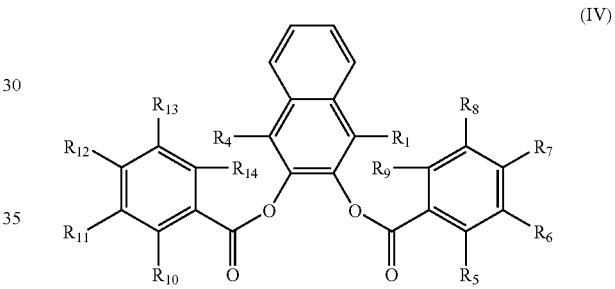

(IV)

$R_1$, $R_4$ and $R_{5-14}$ are the same or different. Each of $R_1$ and $R_4$ is hydrogen. At least one of $R_5$-$R_{14}$ is selected from an unsubstituted hydrocarbyl group having 1 to 20 carbon atoms, a halohydrocarbyl group, a halogen, a silicon-containing hydrocarbyl group, and combinations thereof. $R_7$ and $R_{12}$ are simultaneously not a methyl group.

An advantage of the present disclosure is the provision of substituted phenylene aromatic diester compounds with improved properties.

An advantage of the present disclosure is the provision of improved substituted phenylene aromatic diester suitable for use in procatalyst and/or catalyst compositions for the production of olefin-based polymers.

DETAILED DESCRIPTION

The present disclosure is directed to the production of substituted 1,2-phenylene aromatic diesters.

In an embodiment, a process for producing a diester is provided. The process includes reacting a substituted aromatic diol with an aromatic carboxylic acid or derivative thereof. The reaction forms a substituted phenylene aromatic diester.

As used herein, an "aromatic diol" is a compound containing at least one benzene ring with at least two adjacent hydroxyl groups. It is understood that the aromatic diol may be a monocyclic structure or a polycyclic structure. Nonlimiting examples of suitable aromatic diols include benzenediols such as 1,2-benzenediol (catechol), 1,2-dihydroxynaphthalene, 2,3-dihydroxynaphthalene, and 1,8-dihydroxynaphthalene.

The term "substituted aromatic diol," as used herein, refers to an aromatic diol whereby at least one (or two, or three, or four) of the benzene-ring substituents (other than the two hydroxyl groups) is a substituted hydrocarbyl group having 1 to 20 carbon atoms, an unsubstituted hydrocarbyl group having 1 to 20 carbon atoms, an alkoxy group having 1 to 20 carbon atoms, a heteroatom, and combinations thereof. As used herein, the term "hydrocarbyl" and "hydrocarbon" refer to substituents containing only hydrogen and carbon atoms, including branched or unbranched, saturated or unsaturated, cyclic, polycyclic, fused, or acyclic species, and combinations thereof. Nonlimiting examples of hydrocarbyl groups include alkyl-, cycloalkyl-, alkenyl-, alkadienyl-, cycloalkenyl-, cycloalkadienyl-, aryl-, aralkyl, alkylaryl, and alkynyl- groups.

As used herein, the terms "substituted hydrocarbyl" and "substituted hydrocarbon" refer to a hydrocarbyl group that is substituted with one or more nonhydrocarbyl substituent groups. A nonlimiting example of a nonhydrocarbyl substituent group is a heteroatom. As used herein, a "heteroatom" refers to an atom other than carbon or hydrogen. The heteroatom can be a non-carbon atom from Groups IV, V, VI, and VII of the Periodic Table. Nonlimiting examples of heteroatoms include: halogens (F, Cl, Br, I), N, O, P, B, S, and Si. A substituted hydrocarbyl group also includes a halohydrocarbyl group and/or a silicon-containing hydrocarbyl group. As used herein, the term "halohydrocarbyl group" refers to a hydrocarbyl group that is substituted with one or more halogen atoms. As used herein, the term "silicon-containing hydrocarbyl group" is a hydrocarbyl group that is substituted with one or more silicon atoms. The silicon atom(s) may or may not be in the carbon chain.

An aromatic carboxylic acid, or a derivative of an aromatic carboxylic acid, is another reactant in the present process. As used herein, an "aromatic carboxylic acid" is a compound containing at least one benzene ring with at least one carboxyl group directly bonded to the benzene ring. It is understood that the aromatic carboxylic acid may be a monocyclic structure or a polycyclic structure. The aromatic carboxylic acid may be a mono- or a poly-carboxylic acid. Nonlimiting examples of suitable aromatic carboxylic acids include benzoic acid, 1-naphthoic acid, 2-naphthoic acid, 6H-phenalene-2-carboxylic acid, anthracene-2-carboxylic acid, phenanthrene-2-carboxylic acid, and phenanthrene-3-carboxylic acid.

A "derivative of an aromatic carboxylic acid" or "an aromatic carboxylic acid derivative," as used herein, refers to an aromatic acyl halide, an aromatic anhydride, an aromatic carboxylate salt, or any combination thereof. It is understood that the derivative of the aromatic carboxylic acid may be a monocyclic structure or a polycyclic structure. Nonlimiting examples of suitable aromatic acyl halides include halides of any of the aromatic carboxylic acids disclosed above (i.e., a halide of one or more of the following: benzoic acid, 1-naphthoic acid, 2-naphthoic acid, 6H-phenalene-2-carboxylic acid, anthracene-2-carboxylic acid, phenanthrene-2-carboxylic acid, and/or phenanthrene-3-carboxylic acid). Further nonlimiting examples of suitable aromatic acyl halides include benzoyl chloride, benzoyl fluoride, benzoyl bromide, and benzoyl iodide, naphthoyl chloride, naphthoyl fluoride, naphthoyl bromide, naphthoyl iodide, and any combination of the foregoing aromatic acyl halides.

Nonlimiting examples of suitable aromatic anhydrides include anhydride of the aromatic carboxylic acids disclosed above. (i.e., an anhydride of one or more of the following: benzoic acid, 1-naphthoic acid, 2-naphthoic acid, 6H-phenalene-2-carboxylic acid, anthracene-2-carboxylic acid, phenanthrene-2-carboxylic acid, and/or phenanthrene-3-carboxylic acid). Further nonlimiting examples of suitable aromatic anhydrides include benzoic anhydride and any combination of the foregoing aromatic anhydrides.

Nonlimiting examples of suitable aromatic carboxylate salts include potassium, sodium, or lithium salt of the aromatic carboxylic acids disclosed above (i.e., salts of one or more of the following: benzoic acid, 1-naphthoic acid, 2-naphthoic acid, 6H-phenalene-2-carboxylic acid, anthracene-2-carboxylic acid, phenanthrene-2-carboxylic acid, and/or phenanthrene-3-carboxylic acid). Further nonlimiting examples of suitable aromatic carboxylate salts include potassium benzoate, sodium benzoate, lithium benzoate, potassium 2-naphthoate, sodium 2-naphthoate, and any combination of the foregoing aromatic carboxylate salts.

The aromatic carboxylic acid, or derivative thereof may be substituted. The term "substituted aromatic carboxylic acid or derivative thereof," as used herein, refers to an aromatic carboxylic acid, or derivative thereof, whereby at least one of the benzene-ring substituents (other than the carboxyl group) is a substituted hydrocarbyl group having 1 to 20 carbon atoms, an unsubstituted hydrocarbyl group having 1 to 20 carbon atoms, an alkoxy group having 1 to 20 carbon atoms, a heteroatom, and combinations thereof. Thus, the term "substituted aromatic carboxylic acid or derivative thereof" includes substituted aromatic carboxylic acid, substituted aromatic acyl halide, substituted aromatic anhydride, and/or substituted aromatic carboxylate salt.

In an embodiment, the present process includes reacting the substituted aromatic diol with the aromatic carboxylic acid (or derivative thereof) under reaction conditions to form a substituted phenylene aromatic diester. "Reaction conditions," as used herein, refer to temperature, pressure, reactant concentrations, solvent concentrations, reactant mixing/addition parameters, and/or other conditions that influence the properties of the resulting product.

The characteristics of the phenylene moiety are determined by the substituted aromatic diol. For example, a substituted 1,2-benzenediol yields a substituted 1,2-phenylene aromatic diester. In an embodiment, the substituted aromatic diol is a substituted catechol. The substituted catechol has the structure (I):

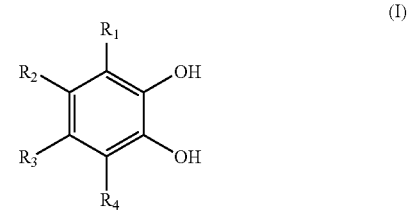

wherein at least one, or two, or three, or four R group(s) of $R_1$-$R_4$ is selected from a substituted hydrocarbyl group having 1 to 20 carbon atoms, an unsubstituted hydrocarbyl group having 1 to 20 carbon atoms, an alkoxy group having 1 to 20 carbon atoms, a heteroatom, and combinations thereof. Each of $R_1$-$R_4$ may or may not be hydrogen. The process includes reacting the substituted catechol with an aromatic acyl halide, such as a benzoyl halide. This reaction forms a substituted 1,2-phenylene dibenzoate of the structure (II):

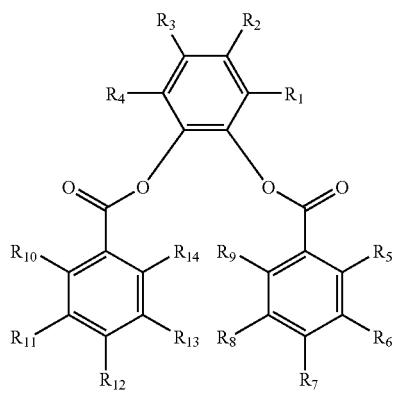

wherein $R_1$-$R_4$ are the same or different. At least one of $R_1$-$R_4$ is selected from a substituted hydrocarbyl group having 1 to 20 carbon atoms, an unsubstituted hydrocarbyl group having 1 to 20 carbon atoms, an alkoxy group having 1 to 20 carbon atoms, a heteroatom, and combinations thereof. Any of $R_1$-$R_4$ may also be hydrogen.

In an embodiment, each R group of $R_1$-$R_4$ that is not hydrogen is an alkyl group having 1 to 20 carbon atoms.

In an embodiment, the process includes reacting a substituted aromatic diol, such as a substituted catechol, with an unsubstituted or substituted aromatic acyl halide under reaction conditions. At least one of $R_1$-$R_4$ of the substituted catechol is selected from an unsubstituted hydrocarbyl group having 2 to 20 carbon atoms or a substituted hydrocarbyl group having 2 to 20 carbon atoms. Each of the other R groups of $R_1$-$R_4$ is hydrogen. The process includes forming a substituted phenylene aromatic diester of structure (II) wherein $R_1$-$R_{14}$ are the same or different. One of $R_1$-$R_4$ of structure (II) is a substituted hydrocarbyl group having 2 to 20 carbon atoms or an unsubstituted hydrocarbyl group having 2 to 20 carbon atoms. Each of the other $R_1$-$R_4$ substituents is hydrogen. Each of $R_5$-$R_{14}$ is hydrogen. In another embodiment, each $R_1$-$R_4$ group(s) that is not hydrogen is an alkyl group having 2 to 20 carbon atoms.

In an embodiment, only one of $R_1$-$R_4$ is substituted with the remaining $R_1$-$R_4$ being hydrogen.

In an embodiment, the process includes selecting a substituted catechol such that neither $R_1$ nor $R_2$ is a methyl group when each of the other R groups of $R_1$-$R_{14}$ is hydrogen.

In an embodiment, the process includes reacting the substituted catechol with a substituted aromatic acyl halide under reaction conditions. The substituted catechol includes one (or two, or three, or four) R groups of $R_1$-$R_4$ selected from an unsubstituted/substituted hydrocarbyl group having 2 to 20 carbon atoms and the remaining R groups of $R_1$-$R_4$ being hydrogen.

In an embodiment, the substituted aromatic acyl halide is a substituted benzoyl halide of the structure (III):

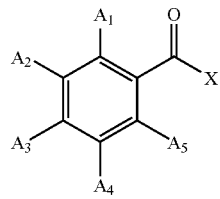

wherein X is a halogen atom (F, Cl, Br, I). At least one (or two, or three, or four, or five) A group(s) of $A_1$-$A_5$ is selected from a substituted hydrocarbyl group having 1 to 20 carbon atoms, an unsubstituted hydrocarbyl group having 1 to 20 carbon atoms, an alkoxy group having 1 to 20 carbon atoms, a heteroatom, and combinations thereof. Any of $A_1$-$A_5$ may also be hydrogen. A nonlimiting example of a suitable substituted aromatic acyl halide is a substituted benzoyl chloride.

The reaction between the substituted catechol and the substituted aromatic acyl halide (III) forms a substituted 1,2-phenylene dibenzoate of the structure (II) wherein $R_1$-$R_{14}$ are the same or different. One of $R_1$-$R_4$ is selected from an unsubstituted or a substituted hydrocarbyl group having 1 to 20 carbon atoms. Each of the other of $R_1$-$R_4$ is hydrogen. $R_5$-$R_{14}$ are the same or different. Each of $R_5$-$R_{14}$ is selected from hydrogen, a substituted or unsubstituted hydrocarbyl group having 1 to 20 carbon atoms, an alkoxy group having 1 to 20 carbon atoms, a halogen, and combinations thereof. In a further embodiment, each R group of $R_1$-$R_{14}$ that is not hydrogen is an alkyl group having 1 to 20 carbon atoms.

The disclosure provides another process. In an embodiment, a process for producing a diester is provided which includes reacting a substituted aromatic diol with a substituted aromatic acyl halide under reaction conditions and forming a substituted 1,2-phenylene dibenzoate of structure (II):

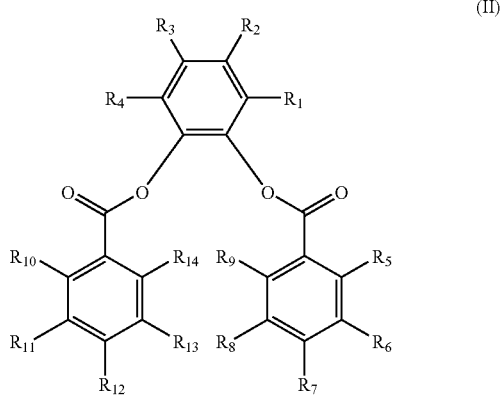

wherein $R_1$-$R_{14}$ are the same or different. At least one (or two, or three, or four) R group(s) of $R_1$-$R_4$, at least one (or two, or three, or four, or five) R group(s) of $R_5$-$R_9$, and at least one (or two, or three, or four, or five) R group(s) of $R_{10}$-$R_{14}$ is selected from a substituted hydrocarbyl group having 1 to 20 carbon atoms, an unsubstituted hydrocarbyl group having 1 to 20 carbon atoms, an alkoxy group having 1 to 20 carbon atoms, a heteroatom, and combinations thereof. Each of $R_1$-$R_{14}$ may or may not be hydrogen. In a further embodiment, each $R_1$-$R_{14}$ group(s) that is not hydrogen is an alkyl group having 1 to 20 carbon atoms.

In an embodiment, the process includes reacting a substituted catechol with a substituted benzoyl halide to form the substituted 1,2-phenylene dibenzoate of structure (II) wherein at least one of $R_1$-$R_4$, at least one of $R_5$-$R_9$, and at least one of $R_{10}$-$R_{14}$ is substituted (i.e., not hydrogen) as disclosed above. In a further embodiment, each $R_1$-$R_{14}$ group(s) that is not hydrogen is an alkyl group having 1 to 20 carbon atoms.

The disclosure provides another process. In an embodiment, a process is provided which includes reacting an aromatic diol with a di-substituted (or tri-, or tetra-, or penta-substituted) aromatic carboxylic acid or derivative thereof under reaction conditions. The aromatic diol may be substituted or unsubstituted. The process includes forming a substituted 1,2-phenylene dibenzoate of the structure (II):

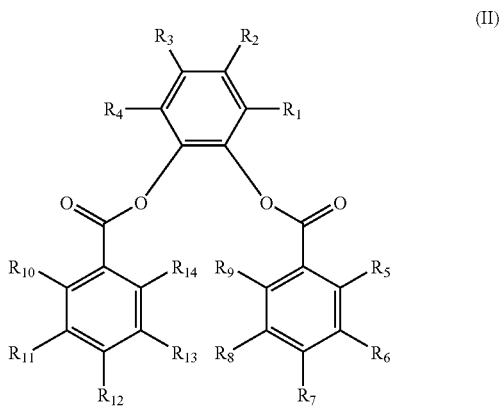

(II)

wherein $R_1$-$R_{14}$ are the same or different. At least two of $R_5$-$R_9$ and at least two of $R_{10}$-$R_{14}$ is selected from an unsubstituted hydrocarbyl group having 1 to 20 carbon atoms, a substituted hydrocarbyl group having 1 to 20 carbon atoms, an alkoxy group having 1 to 20 carbon atoms, a halogen, and combinations thereof. In a further embodiment, each $R_1$-$R_{14}$ group(s) that is not hydrogen is an alkyl group having 1 to 20 carbon atoms.

In an embodiment, the process includes reacting a catechol with a di-substituted (or tri-, or tetra-, or penta-substituted) aromatic acyl halide and forming a substituted 1,2-phenylene dibenzoate of the structure (II) wherein each of $R_1$-$R_4$ is hydrogen, and at least two of $R_5$-$R_9$ and at least two of $R_{10}$-$R_{14}$ are substituted as disclosed above. In a further embodiment, each $R_1$-$R_{14}$ group(s) that is not hydrogen is an alkyl group having 1 to 20 carbon atoms.

In an embodiment, the process includes reacting a substituted aromatic diol with a di-substituted (or tri-, or tetra-, or penta-substituted) aromatic acyl halide to form a substituted phenylene dibenzoate of structure (II) wherein at least one of $R_1$-$R_4$ is selected from an unsubstituted hydrocarbyl group having 1 to 20 carbon atoms, a substituted hydrocarbyl group having 1 to 20 carbon atoms, an alkoxy group having 1 to 20 carbon atoms, and a halogen. At least two of $R_5$-$R_9$ and at least two of $R_{10}$-$R_{14}$ are substituted as disclosed above. In a further embodiment, each R group of $R_1$-$R_{14}$ that is not hydrogen is an alkyl group having 1 to 20 carbon atoms.

The ester groups extending from the phenylene moiety of structure (II) may be considered mirror images of each other. In this sense, a symmetry may exist between the ester groups such that the individual substituents $R_5$-$R_9$ correspond to or otherwise mirror respective individual substituents $R_{10}$-$R_{14}$. As used herein, the term "mated" or "a respective mate" or similar term(s) refers to the following relationships or pairings between substituents $R_5$-$R_9$ and substituents $R_{10}$-$R_{14}$: $R_5$ is mated/paired with $R_{10}$, $R_6$ is mated/paired with $R_{11}$, $R_7$ is mated/paired with $R_{12}$, $R_8$ is mated/paired with $R_{13}$, and $R_9$ is mated/paired with $R_{14}$.

The disclosure provides another process. In an embodiment, a process for producing a diester is provided which includes reacting an aromatic diol with a first aromatic carboxylic acid or derivative thereof and a second aromatic carboxylic acid or derivative thereof under reaction conditions. The aromatic diol may be substituted or may be unsubstituted. The second aromatic carboxylic acid or derivative thereof is different than the first aromatic carboxylic acid or derivative thereof. The process forms a substituted 1,2-phenylene dibenzoate of the structure (II):

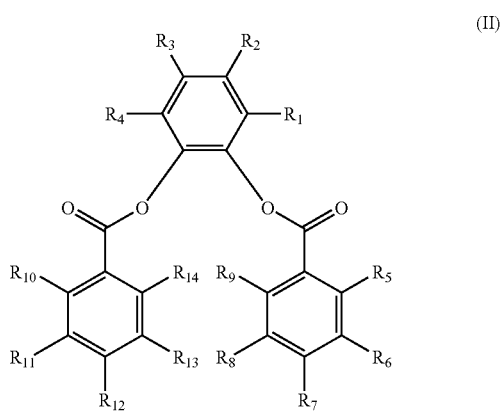

(II)

wherein $R_1$-$R_{14}$ are the same or different. Each of $R_1$-$R_{14}$ is selected from hydrogen, a substituted hydrocarbyl group having 1 to 20 carbon atoms, an unsubstituted hydrocarbyl group having 1 to 20 carbon atoms, a substituted hydrocarbyl group having 1 to 20 carbon atoms, an alkoxy group having 1 to 20 carbon atoms, a halogen, and combinations thereof. At least one of $R_5$-$R_9$ is different than its respective $R_{10}$-$R_{14}$ mate. In a further embodiment, each R group of $R_1$-$R_{14}$ that is not hydrogen is an alkyl group having 1 to 20 carbon atoms.

The reaction between the aromatic diol and the first aromatic carboxylic acid (or derivative thereof) and the second aromatic carboxylic acid (or derivative thereof) may be reacted in any order as desired. In one embodiment, the aromatic diol is reacted with a first aromatic acyl halide. Then a second aromatic acyl halide is added to this diol/acyl halide mixture under reaction conditions. The reaction proceeds to form a substituted 1,2-phenylene dibenzoate wherein at least one of $R_5$-$R_9$ is different than its respective $R_{10}$-$R_{14}$ mate.

In an embodiment, the process includes reacting the aromatic diol with the first aromatic acyl halide and the second aromatic acyl halide different than the first aromatic acyl halide simultaneously, or substantially simultaneously. The process forms a mixture which contains a substituted 1,2-phenylene diester of structure (II) wherein at least one of $R_5$-$R_9$ is different than its respective $R_{10}$-$R_{14}$ mate. The mixture may or may not be separated and used in a catalyst synthesis procedure.

In another nonlimiting example, the first aromatic acyl halide may be a benzoyl halide of structure (III) wherein one substituent, such as substituent $A_1$ is substituted.

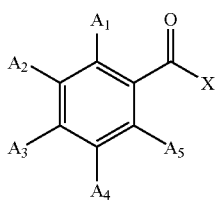

(III)

The second aromatic acyl halide may be a benzoyl halide of structure (III) wherein a substituent other than $A_1$ ($A_3$ for example) is substituted. The process includes reacting the aromatic diol with the first aromatic acyl halide and the second aromatic acyl halide to form a substituted 1,2-phenylene dibenzoate wherein at least one of $R_5$-$R_9$ is different than its respective $R_{10}$-$R_{14}$ mate. For example, the reaction may yield a substituted 1,2-phenylene dibenzoate wherein $R_5$ is not the same substituent as $R_{10}$ and/or $R_7$ is not the same substituent as $R_{12}$.

In any of the foregoing processes the aromatic diol may be a dihydroxynaphthalene. The dihydroxynaphthalene may be substituted or unsubstituted. Similarly, the carboxylic acid derivative of any of the foregoing processes may be a naphthoyl halide. The naphthoyl halide may be substituted or unsubstituted.

The present disclosure provides another process for producing a diester. In an embodiment, a process for producing a diester is provided which includes reacting a dihydroxynaphthalene with a carboxylic acid or derivative thereof under reaction conditions. The dihydroxynaphthalene may be 1,2-dihydroxynaphthalene and/or 2,3-dihydroxynaphthalene. The reaction forms or otherwise produces a 1,2-phenylene dibenzoate of the structure (II):

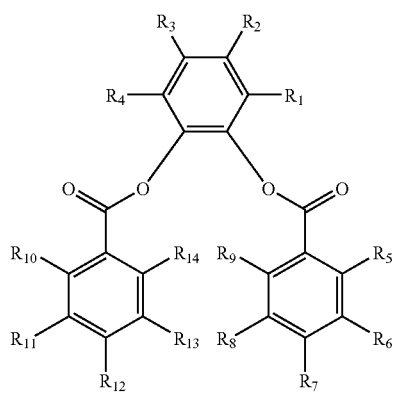

(II)

wherein $R_1$-$R_{14}$ are the same or different. Any consecutive R groups in $R_1$-$R_4$ are members of a $C_6$ aromatic ring. Each of $R_1$-$R_{14}$ may or may not be hydrogen. In a further embodiment, the dihydroxynaphthalene is an unsubstituted or a substituted 2,3-dihydroxynaphthalene. Each of $R_5$-$R_{14}$ is hydrogen. In another embodiment, the dihydroxynaphthalene is a substituted 1,2-dihydroxynaphthalene. Each of $R_5$-$R_{14}$ is hydrogen. In an embodiment, at least one R group of $R_1$-$R_{14}$ that is not a part of a $C_6$ aromatic ring is not hydrogen.

In an embodiment, the process includes reacting an unsubstituted or a substituted 2,3-dihydroxynaphthalene with an aromatic acyl halide and forming a 1,2-phenylene dibenzoate of the structure (IV) below.

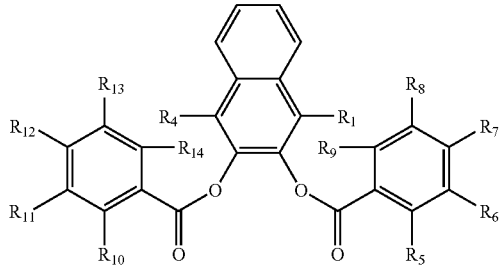

(IV)

The aromatic acyl halide may be substituted or unsubstituted. $R_1$ and $R_4$ are the same or different and each is selected from hydrogen, an unsubstituted hydrocarbyl group having 1 to 20 carbon atoms, a substituted hydrocarbyl group having 1 to 20 carbon atoms, an alkoxy group having 1 to 20 carbon atoms, a halogen, and combinations thereof. In a further embodiment, the aromatic acyl halide is substituted and at least one of $R_5$-$R_{14}$ is selected from an unsubstituted hydrocarbyl group having 1 to 20 carbon atoms, a substituted hydrocarbyl group having 1 to 20 carbon atoms, an alkoxy group having 1 to 20 carbon atoms, a halogen, and combinations thereof.

In an embodiment, the process includes reacting an unsubstituted or substituted 1,2-dihydroxynaphthalene with an aromatic acyl halide and forming a 1,2-phenylene dibenzoate of the structure (V) below.

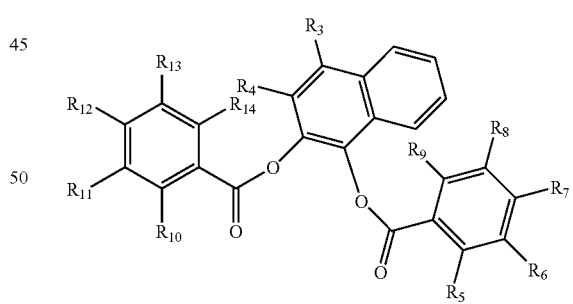

(V)

In an embodiment, the 1,2 dihydroxynaphthalene may be selected such that $R_3$ and $R_4$ are the same or different and each is selected from hydrogen, an unsubstituted hydrocarbyl group having 1 to 20 carbon atoms, a substituted hydrocarbyl group having 1 to 20 carbon atoms, an alkoxy group having 1 to 20 carbon atoms, a halogen, and combinations thereof. The aromatic acyl halide may be substituted such that at least one of $R_5$-$R_{14}$ is selected from an unsubstituted hydrocarbyl group having 1 to 20 carbon atoms, a substituted hydrocarbyl group having 1 to 20 carbon atoms, an alkoxy group having 1 to 20 carbon atoms, a halogen, and combinations thereof.

In an embodiment, the process includes reacting a dihydroxynaphthalene with a naphthoyl halide. The dihydroxynaphthalene may be any dihydroxynaphthalene disclosed herein and may be substituted or unsubstituted. The naphthoyl halide may be any naphthoyl halide disclosed herein and may be substituted or unsubstituted. The reaction forms or otherwise produces a naphthalene dinaphthoate.

The present disclosure provides another process for producing a diester. In an embodiment, a process for producing a diester is provided which includes reacting an aromatic diol with a naphthoyl halide under reaction conditions. The aromatic diol and/or the naphthoyl halide may or may not be substituted. The naphthoyl halide may be a 1-naphthoyl halide and/or a 2-naphthoyl halide. The reaction forms or otherwise produces a 1,2-phenylene dibenzoate of the structure (II):

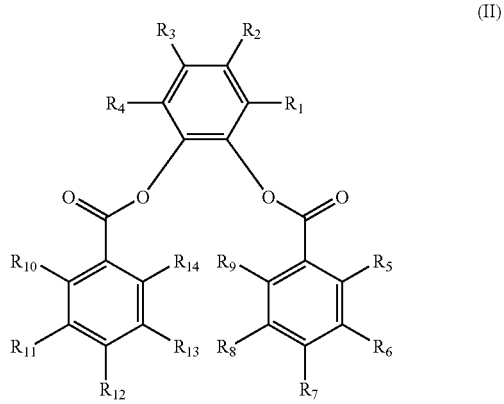

(II)

wherein each of $R_1$-$R_{14}$ may be hydrogen. Any consecutive R groups in $R_5$-$R_9$ and/or in $R_{10}$-$R_{14}$ are members of a $C_6$ aromatic ring.

In an embodiment, the process includes reacting an aromatic diol with a 2-naphthoyl halide under reaction conditions and forming a 1,2-phenylene dibenzoate of the structure (VI).

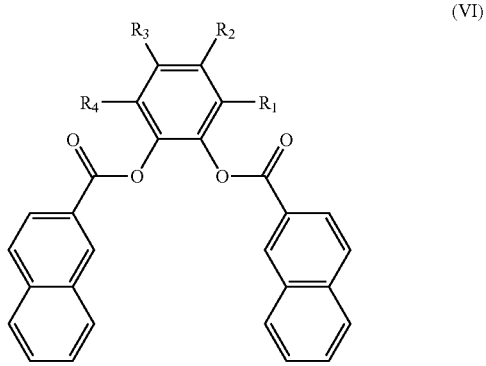

(VI)

In an embodiment, the process includes reacting an aromatic diol with a 1-naphthoyl halide and forming a 1,2-phenylene dibenzoate of the structure (VII).

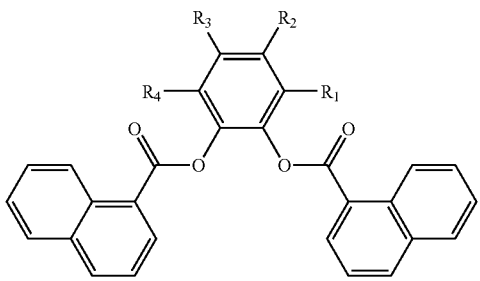

(VII)

In an embodiment, $R_1$-$R_4$ are the same or different and each is selected from hydrogen, an unsubstituted hydrocarbyl group having 1 to 20 carbon atoms, a substituted hydrocarbyl group having 1 to 20 carbon atoms, an alkoxy group having 1 to 20 carbon atoms, a halogen, and combinations thereof.

In another embodiment, the process includes reacting a dihydroxynaphthalene with a naphthoyl halide to form a naphthalene dinaphthoate.

In an embodiment, any process disclosed herein may include introducing a catalyst into the reaction (or reaction mixture) to assist the reaction between the aromatic diol and the aromatic carboxylic acid or derivative thereof. In one embodiment, the process includes reacting (i) an aromatic diol (substituted or unsubstituted), (ii) an aromatic acyl halide (substituted or unsubstituted), and (iii) the catalyst, and forming or otherwise producing a phenylene aromatic diester. Not wishing to be bound by any particular theory, it is believed that the catalyst promotes esterification between the aromatic diol and the aromatic carboxylic acid (or derivative thereof). Nonlimiting examples of suitable catalysts are metal triflates (trifluoromethanesulfonate) such as bismuth triflate and/or inorganic acids such as sulfuric acid.

In an embodiment, the reaction between the substituted/unsubstituted aromatic carboxylic acid (or derivative thereof) and the substituted/unsubstituted aromatic diol as described above is performed in the presence of a base such as an amine and/or a nitrogen-containing heterocyclic aromatic compound. In one embodiment, the base is triethylamine. In another embodiment, the base is pyridine.

In an embodiment, any of the reactions disclosed herein are performed in a liquid medium. Nonlimiting examples of suitable solvents for the liquid medium may be selected from pyridine, tetrahydrofuran, a halohydrocarbon (aliphatic and/or aromatic), hydrocarbon, alcohol, ether, and any combination thereof. In a further embodiment, the liquid reaction medium is a non-aqueous liquid.

In an embodiment, any of the processes disclosed herein may include removing a reaction product from the liquid medium. The reaction product includes any of the substituted phenylene aromatic diesters disclosed herein. Removal of the reaction product from the liquid medium may include one or more of the following procedures: extracting with a different solvent, precipitating, filtrating, concentrating the filtrate, evaporating the liquid medium, crystallizing the substituted phenylene aromatic diester, recrystallizing the substituted phenylene aromatic diester, complexing with a metal salt, and any combination of the foregoing.

Any process may comprise two or more embodiments disclosed herein.

The disclosure provides a composition. In an embodiment, a substituted phenylene aromatic diester of the structure (II) is provided:

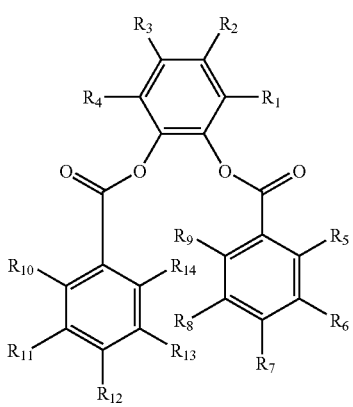

(II)

wherein $R_1$-$R_{14}$ are the same or different. $R_1$ is not an isopropyl group or a tertiary alkyl group. Each of $R_1$ and $R_3$ is selected from an unsubstituted alkyl group having 1 to 20 carbon atoms, an unsubstituted alkenyl group having 1 to 20 atoms, halohydrocarbyl group, a halogen, a silicon-containing hydrocarbyl group, and combinations thereof. Each of $R_2$, $R_4$, and $R_5$-$R_{14}$ is selected from hydrogen, an unsubstituted hydrocarbyl group having 1 to 20 carbon atoms, a halohydrocarbyl group, a halogen, and combinations thereof.

The term "primary alkyl group," as used herein, refers to an alkyl group having 1 to 20 carbon atoms with a carbon atom bonded to a phenyl ring (i.e., a "C-Ph bond"), the carbon atom bonded to one other carbon atom other than the C-Ph bond. A "secondary alkyl group," as used herein, refers to an alkyl group having 1 to 20 carbon atoms with a carbon atom bonded to a phenyl ring, the carbon atom bonded to two other carbon atoms, other than the C-Ph bond. A "tertiary alkyl group," as used herein, refers to an alkyl group having 1 to 20 carbon atoms with a carbon atom bonded to a phenyl ring, the carbon atom bonded to three other carbon atoms, other than the C-Ph bond.

In an embodiment, only atoms selected from C, H, Si, and/or a halogen are bonded to the phenyl moieties at substituent points $R_1$-$R_{14}$ of structure (II).

In an embodiment, each of $R_2$ and $R_4$ is hydrogen. In another embodiment, each of $R_2$, $R_4$, and $R_5$-$R_{14}$ is hydrogen.

In an embodiment, $R_1$ is a methyl group and $R_3$ is a branched alkyl group.

In an embodiment, each of $R_1$ and $R_3$ is selected from a hydrocarbyl group having 2 to 20 carbon atoms.

In an embodiment, any R group of $R_1$-$R_{14}$ that is not a hydrogen is an alkyl group having 1 to 20 carbon atoms.

In an embodiment, each of $R_1$ and $R_3$ is selected from a $C_1$-$C_8$ alkyl group. $R_5$-$R_{14}$ are the same or different and each of $R_5$-$R_{14}$ is selected from hydrogen, a $C_1$-$C_8$ alkyl group, and a halogen. Nonlimiting examples of suitable $C_1$-$C_8$ alkyl groups include methyl, ethyl, n-propyl, isopropyl, n-butyl, i-butyl, and t-butyl, n-pentyl, i-pentyl, neopentyl, t-pentyl, n-hexyl, and 2,4,4-trimethylpentan-2-yl. In a further embodiment, at least one of $R_5$-$R_{14}$ is a $C_1$-$C_8$ alkyl group or a halogen.

In an embodiment, structure (II) includes $R_1$ that is a methyl group and $R_3$ that is a t-butyl group. Each of $R_2$, $R_4$ and $R_5$-$R_{14}$ is hydrogen.

In an embodiment, structure (II) includes $R_1$ and $R_3$, each being an isopropyl group. Each of $R_2$, $R_4$ and $R_5$-$R_{14}$ is hydrogen.

In an embodiment, structure (II) includes each of $R_1$, $R_5$, and $R_{10}$ as a methyl group and $R_3$ is a t-butyl group. Each of $R_2$, $R_4$, $R_6$-$R_9$ and $R_{11}$-$R_{14}$ is hydrogen.

In an embodiment, structure (II) includes each of $R_1$, $R_7$, and $R_{12}$ as a methyl group and $R_3$ is a t-butyl group. Each of $R_2$, $R_4$, $R_5$, $R_6$, $R_8$, $R_9$, $R_{10}$, $R_{11}$, $R_{13}$, and $R_{14}$ is hydrogen.

In an embodiment, structure (II) includes $R_1$ as a methyl group and $R_3$ is a t-butyl group. Each of $R_7$ and $R_{12}$ is an ethyl group. Each of $R_2$, $R_4$, $R_5$, $R_6$, $R_8$, $R_9$, $R_{10}$, $R_{11}$, $R_{13}$, and $R_{14}$ is hydrogen.

In an embodiment, structure (II) includes each of $R_1$, $R_5$, $R_7$, $R_9$, $R_{10}$, $R_{12}$, and $R_{14}$ as a methyl group and $R_3$ is a t-butyl group. Each of $R_2$, $R_4$, $R_6$, $R_8$, $R_{11}$, and $R_{13}$ is hydrogen.

In an embodiment, structure (II) includes $R_1$ as a methyl group and $R_3$ is a t-butyl group. Each of $R_5$, $R_7$, $R_9$, $R_{10}$, $R_{12}$, and $R_{14}$ is an i-propyl group. Each of $R_2$, $R_4$, $R_6$, $R_8$, $R_{11}$, and $R_{13}$ is hydrogen.

In an embodiment, structure (II) includes $R_1$ that is a methyl group and $R_3$ is a t-butyl group. Each of $R_7$ and $R_{12}$ is an ethoxy group. Each of $R_2$, $R_4$, $R_5$, $R_6$, $R_8$, $R_9$, $R_{10}$, $R_{11}$, $R_{13}$, and $R_{14}$ is hydrogen.

In an embodiment, structure (II) includes $R_1$ that is a methyl group and $R_3$ is a t-butyl group. Each of $R_7$ and $R_{12}$ is a fluorine atom. Each of $R_2$, $R_4$, $R_5$, $R_6$, $R_8$, $R_9$, $R_{10}$, $R_{11}$, $R_{13}$, and $R_{14}$ is hydrogen.

In an embodiment, structure (II) includes $R_1$ that is a methyl group and $R_3$ is a t-butyl group. Each of $R_7$ and $R_{12}$ is a chlorine atom. Each of $R_2$, $R_4$, $R_5$, $R_6$, $R_8$, $R_9$, $R_{10}$, $R_{11}$, $R_{13}$, and $R_{14}$ is hydrogen.

In an embodiment, structure (II) includes $R_1$ that is a methyl group and $R_3$ is a t-butyl group. Each of $R_7$ and $R_{12}$ is a bromine atom. Each of $R_2$, $R_4$, $R_5$, $R_6$, $R_8$, $R_9$, $R_{10}$, $R_{11}$, $R_{13}$, and $R_{14}$ is hydrogen.

In an embodiment, structure (II) includes $R_1$ that is a methyl group and $R_3$ is a t-butyl group. Each of $R_7$ and $R_{12}$ is an iodine atom. Each of $R_2$, $R_4$, $R_5$, $R_6$, $R_8$, $R_9$, $R_{10}$, $R_{11}$, $R_{13}$, and $R_{14}$ is hydrogen.

In an embodiment, structure (II) includes $R_1$ that is a methyl group and $R_3$ is a t-butyl group. Each of $R_6$, $R_7$, $R_{11}$, and $R_{12}$ is a chlorine atom. Each of $R_2$, $R_4$, $R_5$, $R_8$, $R_9$, $R_{10}$, $R_{13}$, and $R_{14}$ is hydrogen.

In an embodiment, structure (II) includes $R_1$ that is a methyl group and $R_3$ is a t-butyl group. Each of $R_6$, $R_8$, $R_{11}$, and $R_{13}$ is a chlorine atom. Each of $R_2$, $R_4$, $R_5$, $R_7$, $R_9$, $R_{10}$, $R_{12}$, and $R_{14}$ is hydrogen.

In an embodiment, structure (II) includes $R_1$ that is a methyl group and $R_3$ is a t-butyl group. Each of is $R_2$ and $R_4$ is hydrogen. Each of $R_5$-$R_{14}$ is a fluorine atom.

In an embodiment, structure (II) includes $R_1$ that is a methyl group and $R_3$ is a t-butyl group. Each of $R_7$ and $R_{12}$ is a trifluoromethyl group. Each of $R_2$, $R_4$, $R_5$, $R_6$, $R_8$, $R_9$, $R_{10}$, $R_{11}$, $R_{13}$, and $R_{14}$ is hydrogen.

In an embodiment, structure (II) includes $R_1$ that is a methyl group and $R_3$ is a t-butyl group. Each of $R_7$ and $R_{12}$ is an ethoxycarbonyl group. Each of $R_2$, $R_4$, $R_5$, $R_6$, $R_8$, $R_9$, $R_{10}$, $R_{11}$, $R_{13}$, and $R_{14}$ is hydrogen.

In an embodiment, structure (II) includes $R_1$ that is a methyl group and $R_3$ is a t-butyl group. Each of $R_7$ and $R_{12}$ is a diethylamino group. Each of $R_2$, $R_4$, $R_5$, $R_6$, $R_8$, $R_9$, $R_{10}$, $R_{11}$, $R_{13}$, and $R_{14}$ is hydrogen.

In an embodiment, structure (II) includes $R_1$ that is a methyl group and $R_3$ is a 2,4,4-trimethylpentan-2-yl group. Each of $R_2$, $R_4$ and $R_5$-$R_{14}$ is hydrogen.

In an embodiment, structure (II) includes $R_1$ and $R_3$, each of which is a sec-butyl group. Each of $R_2$, $R_4$ and $R_5$-$R_{14}$ is hydrogen.

In an embodiment, structure (II) includes $R_3$ is that a 2,4,4-trimethylpentan-2-yl group.

In an embodiment, structure (II) includes one of $R_7$ and $R_{12}$ is an alkyl group having 1 to 6 carbon atoms or a halogen atom.

In an embodiment, structure (II) includes each of $R_7$ and $R_{12}$ is a methyl group and each of $R_5$-$R_6$, $R_8$-$R_{11}$, and $R_{13}$-$R_{14}$ is hydrogen.

In an embodiment, structure (II) includes each of $R_7$ and $R_{12}$ is a fluorine atom or a chlorine atom and each of $R_5$-$R_6$, $R_8$-$R_{11}$, and $R_{13}$-$R_{14}$ is hydrogen.

Nonlimiting examples of suitable substituted 1,2-phenylene dibenzoate include the following compounds as well as their derivatives with $R_5$-$R_{14}$ substitution(s) as defined above: 3,5-dimethyl-1,2-phenylene dibenzoate; 5-ethyl-3-methyl-1,2-phenylene dibenzoate; 3-methyl-5-propyl-1,2-phenylene dibenzoate; 5-isopropyl-3-methyl-1,2-phenylene dibenzoate; 5-butyl-3-methyl-1,2-phenylene dibenzoate; 5-isobutyl-3-methyl-1,2-phenylene dibenzoate; 5-tert-butyl-3-methyl-1,2-phenylene dibenzoate; 5-cyclopentyl-3-methyl-1,2-phenylene dibenzoate; 5-cyclohexyl-3-methyl-1,2-phenylene dibenzoate; 3-methyl-5-(2,4,4-trimethylpentan-2-yl)-1,2-phenylene dibenzoate; 5-methylbiphenyl-3,4-diyl dibenzoate; 3-ethyl-5-methyl-1,2-phenylene dibenzoate; 3,5-diethyl-1,2-phenylene dibenzoate; 3-ethyl-5-propyl-1,2-phenylene dibenzoate; 3-ethyl-5-isopropyl-1,2-phenylene dibenzoate; 5-butyl-3-ethyl-1,2-phenylene dibenzoate; 3-ethyl-5-isobutyl-1,2-phenylene dibenzoate; 5-tert-butyl-3-ethyl-1,2-phenylene dibenzoate; 5-cyclopentyl-3-ethyl-1,2-phenylene dibenzoate; 5-cyclohexyl-3-ethyl-1,2-phenylene dibenzoate; 3-ethyl-5-(2,4,4-trimethylpentan-2-yl)-1,2-phenylene dibenzoate; 5-ethylbiphenyl-3,4-diyl dibenzoate; 5-methyl-3-propyl-1,2-phenylene dibenzoate; 5-ethyl-3-propyl-1,2-phenylene dibenzoate; 3,5-dipropyl-1,2-phenylene dibenzoate; 5-isopropyl-3-propyl-1,2-phenylene dibenzoate; 5-butyl-3-propyl-1,2-phenylene dibenzoate; 5-isobutyl-3-propyl-1,2-phenylene dibenzoate; 5-tert-butyl-3-propyl-1,2-phenylene dibenzoate; 5-cyclopentyl-3-propyl-1,2-phenylene dibenzoate; 5-cyclohexyl-3-propyl-1,2-phenylene dibenzoate; 3-propyl-5-(2,4,4-trimethylpentan-2-yl)-1,2-phenylene dibenzoate; 5-propylbiphenyl-3,4-diyl dibenzoate; 3-isopropyl-5-methyl-1,2-phenylene dibenzoate; 5-ethyl-3-isopropyl-1,2-phenylene dibenzoate; 3-isopropyl-5-propyl-1,2-phenylene dibenzoate; 3,5-diisopropyl-1,2-phenylene dibenzoate; and/or 5-butyl-3-isopropyl-1,2-phenylene dibenzoate; 5-isobutyl-3-isopropyl-1,2-phenylene dibenzoate; 5-tert-butyl-3-isopropyl-1,2-phenylene dibenzoate; 5-cyclopentyl-3-isopropyl-1,2-phenylene dibenzoate; 5-cyclohexyl-3-isopropyl-1,2-phenylene dibenzoate; 3-isopropyl-5-(2,4,4-trimethylpentan-2-yl)-1,2-phenylene dibenzoate; 5-isopropylbiphenyl-3,4-diyl dibenzoate; 3-butyl-5-methyl-1,2-phenylene dibenzoate; 3-butyl-5-ethyl-1,2-phenylene dibenzoate; 3-butyl-5-propyl-1,2-phenylene dibenzoate; 3-butyl-5-isopropyl-1,2-phenylene dibenzoate; 3,5-dibutyl-1,2-phenylene dibenzoate; 3-butyl-5-isobutyl-1,2-phenylene dibenzoate; 5-tert-butyl-3-butyl-1,2-phenylene dibenzoate; 3-butyl-5-cyclopentyl-1,2-phenylene dibenzoate; 3-butyl-5-cyclohexyl-1,2-phenylene dibenzoate; 3-butyl-5-(2,4,4-trimethylpentan-2-yl)-1,2-phenylene dibenzoate; 5-butylbiphenyl-3,4-diyl dibenzoate; 3-isobutyl-5-methyl-1,2-phenylene dibenzoate; 5-ethyl-3-isobutyl-1,2-phenylene dibenzoate; 3-isobutyl-5-propyl-1,2-phenylene dibenzoate; 3-isobutyl-5-isopropyl-1,2-phenylene dibenzoate; 5-butyl-3-isobutyl-1,2-phenylene dibenzoate; 3,5-diisobutyl-1,2-phenylene dibenzoate; 5-tert-butyl-3-isobutyl-1,2-phenylene dibenzoate; 3-isobutyl-5-(2,4,4-trimethylpentan-2-yl)-1,2-phenylene dibenzoate; 5-isobutylbiphenyl-3,4-diyl dibenzoate; 3-cyclopentyl-5-methyl-1,2-phenylene dibenzoate; 3-cyclopentyl-5-ethyl-1,2-phenylene dibenzoate; 3-cyclopentyl-5-propyl-1,2-phenylene dibenzoate; 3-cyclopentyl-5-isopropyl-1,2-phenylene dibenzoate; 5-butyl-3-cyclopentyl-1,2-phenylene dibenzoate; 3-cyclopentyl-5-isobutyl-1,2-phenylene dibenzoate; 5-tert-butyl-3-cyclopentyl-1,2-phenylene dibenzoate; 3,5-dicyclopentyl-1,2-phenylene dibenzoate; 5-cyclohexyl-3-cyclopentyl-1,2-phenylene dibenzoate; 3-cyclopentyl-5-(2,4,4-trimethylpentan-2-yl)-1,2-phenylene dibenzoate; 5-cyclopentylbiphenyl-3,4-diyl dibenzoate; 3-cyclohexyl-5-methyl-1,2-phenylene dibenzoate; 3-cyclohexyl-5-ethyl-1,2-phenylene dibenzoate; 3-cyclohexyl-5-propyl-1,2-phenylene dibenzoate; 3-cyclohexyl-5-isopropyl-1,2-phenylene dibenzoate; 5-butyl-3-cyclohexyl-1,2-phenylene dibenzoate; 3-cyclohexyl-5-isobutyl-1,2-phenylene dibenzoate; 5-tert-butyl-3-cyclohexyl-1,2-phenylene dibenzoate; 3-cyclohexyl-5-cyclopentyl-1,2-phenylene dibenzoate; 3,5-dicyclohexyl-1,2-phenylene dibenzoate; 3-cyclohexyl-5-(2,4,4-trimethylpentan-2-yl)-1,2-phenylene dibenzoate; 5-cyclohexylbiphenyl-3,4-diyl dibenzoate; 5-methylbiphenyl-2,3-diyl dibenzoate; 5-ethylbiphenyl-2,3-diyl dibenzoate; 5-propylbiphenyl-2,3-diyl dibenzoate; 5-isopropylbiphenyl-2,3-diyl dibenzoate; 5-butylbiphenyl-2,3-diyl dibenzoate; 5-isobutylbiphenyl-2,3-diyl dibenzoate; 5-tert-butylbiphenyl-2,3-diyl dibenzoate; 5-cyclopentylbiphenyl-2,3-diyl dibenzoate; 5-cyclohexylbiphenyl-2,3-diyl dibenzoate; 5-(2,4,4-trimethylpentan-2-yl)biphenyl-2,3-diyl dibenzoate; and/or 3,5-diphenyl-1,2-phenylene dibenzoate.

The present disclosure provides another composition. In an embodiment, a substituted phenylene aromatic diester of the structure (II) is provided:

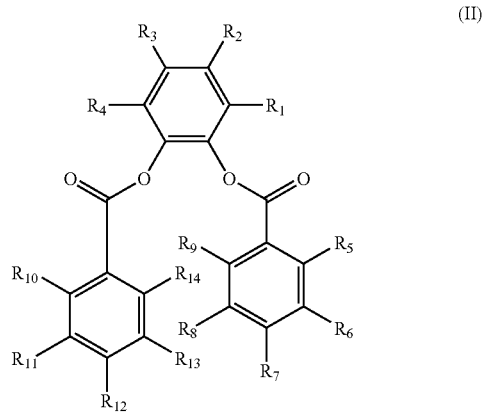

wherein $R_1$-$R_{14}$ are the same or different, $R_2$ is an alkyl group having 2 to 20 carbon atoms and each of the other R groups of $R_1$-$R_4$ is hydrogen. Each of $R_5$-$R_{14}$ is selected from hydrogen, an unsubstituted hydrocarbyl group having 1 to 20 carbon atoms, a halohydrocarbyl group, a halogen, a silicon-containing hydrocarbyl group, and combinations thereof. Each of $R_2$, $R_7$, and $R_{12}$ is simultaneously not a t-butyl group.

In an embodiment, $R_2$ is selected from of a t-butyl group and a 2,4,4-trimethylpentan-2-yl group.

In an embodiment, one of $R_7$ and $R_{12}$ is an alkyl group having 1 to 6 carbon atoms or a halogen atom.

In an embodiment, each of $R_7$ and $R_{12}$ is methyl group and each of $R_5$-$R_6$, $R_8$-$R_{11}$, and $R_{13}$-$R_{14}$ is hydrogen.

In an embodiment, each of $R_7$ and $R_{12}$ is fluorine or chlorine. Each of $R_5$-$R_6$, $R_8$-$R_{11}$, and $R_{13}$-$R_{14}$ is hydrogen.

The present disclosure provides another composition. In an embodiment, a substituted phenylene aromatic diester of the structure (II) is provided:

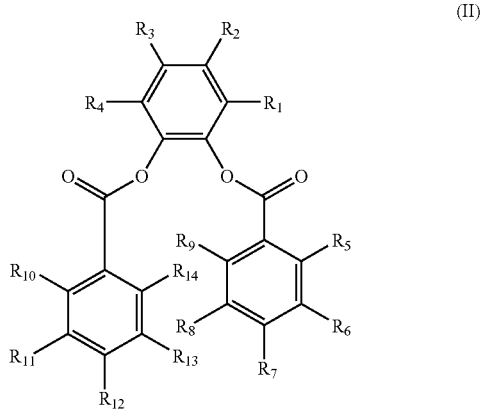

wherein $R_1$-$R_{14}$ are the same or different. Each of $R_1$, $R_3$, $R_4$ is hydrogen, $R_2$ is a hydrocarbyl group having 1 to 20 carbon atoms. At least one of $R_7$ and $R_{12}$ is a halogen or a primary or secondary hydrocarbyl group having 1 to 20 carbon atoms which may optionally be substituted with halogen, silicon, or an alkoxy group. Each of $R_5$-$R_6$, $R_8$-$R_{11}$ and $R_{13}$-$R_{14}$ is selected from hydrogen, an unsubstituted hydrocarbyl group having 1 to 20 carbon atoms, a halohydrocarbyl group, a halogen, a silicon-containing hydrocarbyl group, and combinations thereof.

In an embodiment, $R_2$ is an alkyl group having 1 to 20 carbon atoms.

In an embodiment, each of $R_7$ and $R_{12}$ is a halogen or an alkyl group having 1 to 6 carbon atoms.

In an embodiment, $R_2$ is a methyl group. Each of $R_7$ and $R_{12}$ is a halogen or methyl group. The remaining R groups are hydrogen.

In an embodiment, each of $R_2$ and $R_4$ is a methyl group. Each of $R_7$ and $R_{12}$ is a halogen or a methyl group. The remaining R groups are hydrogen.

The present disclosure provides another composition. In an embodiment, a substituted phenylene aromatic diester of the structure (II) is provided:

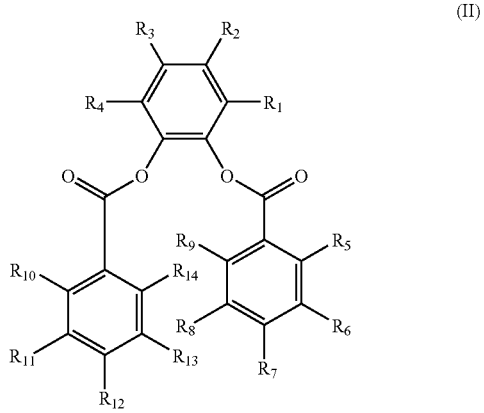

wherein $R_1$-$R_{14}$ are the same or different. $R_1$ is an unsubstituted hydrocarbyl group having 1 to 20 carbon atoms. $R_2$-$R_4$ are selected from hydrogen, an unsubstituted hydrocarbyl group having 1 to 20 carbon atoms, a halohydrocarbyl group, a halogen, a silicon-containing hydrocarbyl group, and combinations thereof. Each of $R_5$-$R_{14}$ is selected from an unsubstituted hydrocarbyl group having 1 to 20 carbon atoms, a halohydrocarbyl group, a halogen, a silicon-containing hydrocarbyl group, and combinations thereof.

The present disclosure provides another composition. In an embodiment, a substituted phenylene aromatic diester of the structure (II) is provided:

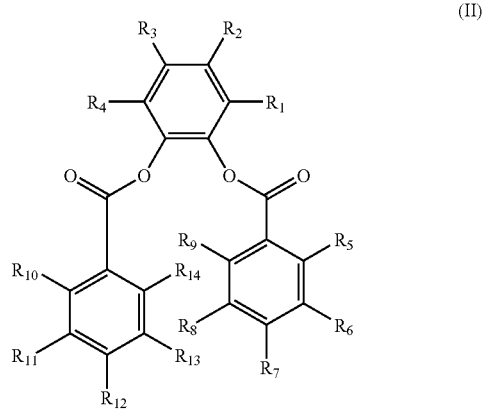

wherein $R_1$-$R_{14}$ are the same or different. $R_2$ is an alkyl group having 2 to 20 carbon atoms. Each other R group of $R_1$-$R_4$ is hydrogen. Each of $R_5$-$R_{14}$ is selected from hydrogen, an unsubstituted hydrocarbyl group having 1 to 20 carbon atoms, a halohydrocarbyl group, a halogen, a silicon-containing hydrocarbyl group, and combinations thereof. $R_2$, $R_7$, and $R_{12}$ are not simultaneously a t-butyl group. In other words, when $R_2$ is a t-butyl group $R_7$ and $R_{12}$ are not a t-butyl group (or when $R_7$ is a t-butyl group; $R_2$ and $R_{12}$ are not a t-butyl group; or when $R_{12}$ is a t-butyl group, $R_2$ and $R_7$ are not a t-butyl group).

In an embodiment, structure (II) includes $R_2$ that is ethyl and each of $R_5$-$R_{14}$ is hydrogen.

In an embodiment, structure (II) includes $R_2$ that is t-butyl and each of $R_5$-$R_{14}$ is hydrogen.

In an embodiment, structure (II) includes $R_2$ that is 2,4,4-trimethylpentan-2-yl and each of $R_5$-$R_{14}$ is hydrogen.

Nonlimiting examples of suitable substituted 1,2-phenylene dibenzoate include 4-ethyl-1,2-phenylene dibenzoate; 4-propyl-1,2-phenylene dibenzoate; 4-isopropyl-1,2-phenylene dibenzoate; 4-butyl-1,2-phenylene dibenzoate; 4-isobutyl-1,2-phenylene dibenzoate; 4-cyclopentyl-1,2-phenylene dibenzoate; 4-cyclohexyl-1,2-phenylene dibenzoate; 4-(2,4,4-trimethylpentan-2-yl)-1,2-phenylene dibenzoate; and/or biphenyl-3,4-diyl dibenzoate.

In an embodiment, two or more of $R_1$-$R_4$ are substituted. Each of the substituted R groups of $R_1$-$R_4$ is selected from an unsubstituted hydrocarbyl group having 2 to 20 carbon atoms. $R_1$ is not a tertiary alkyl group.

The present disclosure provides another composition. In an embodiment, a substituted phenylene aromatic diester is provided. The substituted 1,2-phenylene aromatic diester has the structure (II) below.

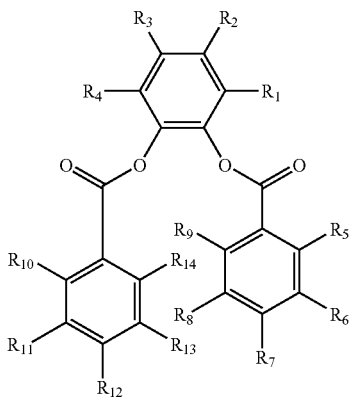

(II)

$R_1$-$R_{14}$ are the same or different. Each of $R_1$, $R_3$, $R_4$ is hydrogen. $R_2$ is a hydrocarbyl group having 1 to 20 carbon atoms. At least one of $R_7$ and $R_{12}$ is a halogen. Each of $R_5$-$R_6$, $R_8$-$R_{11}$ and $R_{13}$-$R_{14}$ is selected from hydrogen, an unsubstituted hydrocarbyl group having 1 to 20 carbon atoms, a halohydrocarbyl group, a halogen, a silicon-containing hydrocarbyl group, and combinations thereof.

In an embodiment, only atoms selected from C, H, Si, and/or a halogen are bonded to the phenyl groups at substituent points $R_1$-$R_{14}$ of structure (II).

In an embodiment, $R_2$ is an alkyl group having 1 to 20 carbon atoms.

In an embodiment, each of $R_7$ and $R_{12}$ is a halogen. In a further embodiment, each of $R_5$, $R_7$, $R_{10}$, and $R_{12}$ is a halogen.

In an embodiment, structure (II) includes $R_2$ that is methyl and $R_7$ and $R_{12}$ that are chlorine. Each other R-group of $R_1$-$R_{14}$ groups is hydrogen.

In an embodiment, structure (II) includes $R_2$ that is t-butyl and $R_7$ and $R_{12}$ that are chlorine. Each other R-group of $R_1$-$R_{14}$ groups is hydrogen.

The disclosure provides another composition. In an embodiment, a substituted phenylene aromatic diester is provided having the structure (II):

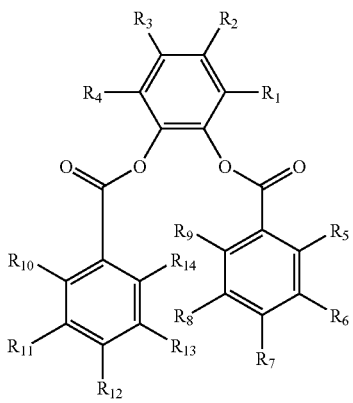

(II)

wherein $R_1$-$R_{14}$ are the same or different. Each of $R_1$, $R_3$, $R_4$ is hydrogen. $R_2$ is a hydrocarbyl group having 1 to 20 carbon atoms. Each of $R_5$-$R_{14}$ is selected from hydrogen, an unsubstituted hydrocarbyl group having 1 to 20 carbon atoms, a halohydrocarbyl group, a halogen, a silicon-containing hydrocarbyl group, and combinations thereof. At least one of $R_5$-$R_6$, $R_8$-$R_{11}$ and $R_{13}$-$R_{14}$ is selected from a $C_1$-$C_6$ alkyl group, a halogen, and combinations thereof.

In an embodiment, only atoms selected from C, H, Si, and/or a halogen are bonded to the phenyl groups at substituent points $R_1$-$R_{14}$ of structure (II).

In an embodiment, $R_2$ is an alkyl group having 1 to 20 carbon atoms.

In an embodiment, each of $R_7$ and $R_{12}$ is a methyl group. In a further embodiment, each of $R_5$, $R_7$, $R_{10}$, and $R_{12}$ is a methyl group.

In an embodiment, structure (II) includes each of $R_2$, $R_7$ and $R_{12}$ as a methyl group. Each other R group of $R_1$-$R_{14}$ is hydrogen.

In an embodiment, structure (II) includes $R_2$ that is t-butyl group and each of $R_7$ and $R_{12}$ is a methyl group. Each other R group of $R_1$-$R_{14}$ is hydrogen.

In an embodiment, structure (II) includes $R_2$ that is a methyl group and each of $R_7$ and $R_{12}$ is a dimethylamino group. Each other R group of $R_1$-$R_{14}$ is hydrogen.

In an embodiment, structure (II) includes $R_2$ that is a t-butyl group and each of $R_7$ and $R_{12}$ is a dimethylamino group. Each other R group of $R_1$-$R_{14}$ is hydrogen.

Nonlimiting examples of suitable substituted 1,2-phenylene dibenzoate include 3-ethyl-1,2-phenylene dibenzoate; 3-propyl-1,2-phenylene dibenzoate; 3-isopropyl-1,2-phenylene dibenzoate; 3-butyl-1,2-phenylene dibenzoate; 3-isobutyl-1,2-phenylene dibenzoate; 3-cyclopentyl-1,2-phenylene dibenzoate; 3-cyclohexyl-1,2-phenylene dibenzoate; 3-cyclohexyl-1,2-phenylene dibenzoate; 3-(2,4,4-trimethylpentan-2-yl)-1,2-phenylene dibenzoate, and/or biphenyl-2,3-diyl dibenzoate.

The disclosure provides another composition. In an embodiment, a substituted 1,2-phenylene aromatic diester of the structure (II) is provided:

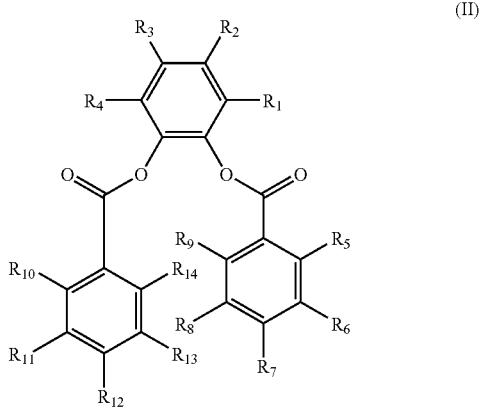

(II)

wherein $R_1$-$R_{14}$ are the same or different. $R_1$ is not a secondary alkyl group or a tertiary alkyl group. Each of $R_1$ and $R_4$ is selected from an unsubstituted alkyl group having 2 to 20 carbon atoms, an unsubstituted alkenyl group having 2 to 20 carbon atoms, a halohydrocarbyl group, a halogen, a silicon-containing hydrocarbyl group, and combinations thereof. Each of $R_2$-$R_3$ and each of $R_5$-$R_{14}$ is selected from hydrogen, unsubstituted hydrocarbyl group having 1 to 20 carbon atoms, a halohydrocarbyl group, a halogen, a silicon-containing hydrocarbyl group, and combinations thereof.

In an embodiment, structure (II) includes $R_2$ and $R_3$ that are each a hydrogen.

In an embodiment, structure (II) includes $R_1$, $R_3$, and $R_4$, each of which is an i-propyl group. Each of $R_2$, $R_5$-$R_9$ and $R_{10}$-$R_{14}$ is hydrogen.

Nonlimiting examples of suitable substituted 1,2-phenylene dibenzoate include the following compounds as well as their derivatives with $R_5$-$R_{14}$ substitution(s) as defined above: 3-ethyl-6-methyl-1,2-phenylene dibenzoate; 3-methyl-6-propyl-1,2-phenylene dibenzoate; 3-butyl-6-methyl-1,2-phenylene dibenzoate; 3-isobutyl-6-methyl-1,2-phenylene dibenzoate; 3-cyclopentyl-6-methyl-1,2-phenylene dibenzoate; 3-cyclohexyl-6-methyl-1,2-phenylene dibenzoate; 4-methylbiphenyl-2,3-diyl dibenzoate; 3,6-diethyl-1,2-phenylene dibenzoate; 3-ethyl-6-propyl-1,2-phenylene dibenzoate; 3-ethyl-6-isopropyl-1,2-phenylene dibenzoate; 3-butyl-6-ethyl-1,2-phenylene dibenzoate; 3-ethyl-6-isobutyl-1,2-phenylene dibenzoate; 3-cyclopentyl-6-ethyl-1,2-phenylene dibenzoate; 3-cyclohexyl-6-ethyl-1,2-phenylene dibenzoate; 4-ethylbiphenyl-2,3-diyl dibenzoate; 3,6-dipropyl-1,2-phenylene dibenzoate; 3-isopropyl-6-propyl-1,2-phenylene dibenzoate; 3-butyl-6-propyl-1,2-phenylene dibenzoate; 3-isobutyl-6-propyl-1,2-phenylene dibenzoate; 3-cyclopentyl-6-propyl-1,2-phenylene dibenzoate; 3-cyclohexyl-6-propyl-1,2-phenylene dibenzoate; 4-propylbiphenyl-2,3-diyl dibenzoate; 3,6-diisopropyl-1,2-phenylene dibenzoate; 3-butyl-6-isopropyl-1,2-phenylene dibenzoate; 3-isobutyl-6-isopropyl-1,2-phenylene dibenzoate; 3-cyclopentyl-6-isopropyl-1,2-phenylene dibenzoate; 3-cyclohexyl-6-isopropyl-1,2-phenylene dibenzoate; 4-isopropylbiphenyl-2,3-diyl dibenzoate; 3,6-dibutyl-1,2-phenylene dibenzoate; 3-butyl-6-isobutyl-1,2-phenylene dibenzoate; 3-butyl-6-cyclopentyl-1,2-phenylene dibenzoate; 3-butyl-6-cyclohexyl-1,2-phenylene dibenzoate; 4-butylbiphenyl-2,3-diyl dibenzoate; 3,6-diisobutyl-1,2-phenylene dibenzoate; 3-cyclopentyl-6-isobutyl-1,2-phenylene dibenzoate; 3-cyclohexyl-6-isobutyl-1,2-phenylene dibenzoate; 4-isobutylbiphenyl-2,3-diyl dibenzoate; 3,6-dicyclopentyl-1,2-phenylene dibenzoate; 3-cyclohexyl-6-cyclopentyl-1,2-phenylene dibenzoate; 4-cyclopentylbiphenyl-2,3-diyl dibenzoate; 3,6-dicyclohexyl-1,2-phenylene dibenzoate; 4-cyclohexylbiphenyl-2,3-diyl dibenzoate; and/or 3,6-phenyl-1,2-phenylene dibenzoate.

The disclosure provides another composition. In an embodiment, a substituted 1,2-phenylene aromatic diester of the structure (II) is provided:

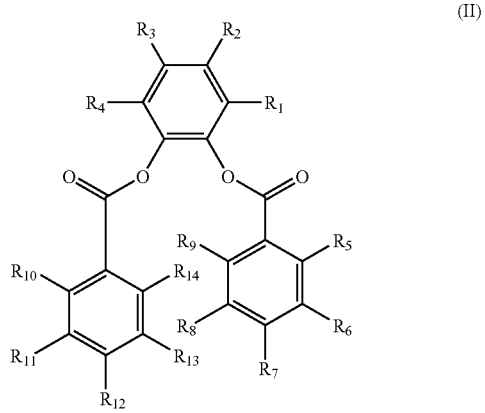

(II)

wherein $R_1$-$R_{14}$ are the same or different. Each of $R_1$, $R_2$, and $R_4$ is selected from an alkyl group having 2 to 20 carbon atoms, an alkenyl group having 2 to 20 carbon atoms, a halohydrocarbyl group, a silicon-containing hydrocarbyl group, and combinations thereof. Each of $R_5$-$R_{14}$ is selected from hydrogen, an unsubstituted hydrocarbyl group having 1 to 20 carbon atoms, a halohydrocarbyl group, a halogen, a silicon-containing hydrocarbyl group, and combinations thereof.

In an embodiment, each of $R_1$, $R_2$, and $R_4$ is selected from an alkyl group having 2 to 20 carbon atoms, an alkenyl group having 2 to 20 carbon atoms, a halohydrocarbyl group, a silicon-containing hydrocarbyl group, and combinations thereof.

In an embodiment, $R_3$ is hydrogen. Each of $R_1$, $R_2$, and $R_4$ is selected from a hydrocarbon group having 2 to 20 carbon atoms. Each of $R_1$ and $R_4$ is not a tertiary alkyl group. Each of $R_5$-$R_{14}$ is selected from hydrogen, an unsubstituted hydrocarbyl group having 1 to 20 carbon atoms, a halohydrocarbyl group, a halogen, a silicon-containing hydrocarbyl group, and combinations thereof.

Nonlimiting examples of suitable substituted 1,2-phenylene dibenzoate include the following compounds as well as their derivatives with $R_5$-$R_{14}$ substitution(s) as defined above: 3,4,6-trimethyl-1,2-phenylene dibenzoate; 3-ethyl-4,6-dimethyl-1,2-phenylene dibenzoate; 4,6-dimethyl-3-propyl-1,2-phenylene dibenzoate; 3-isopropyl-4,6-dimethyl-1,2-phenylene dibenzoate; 3-butyl-4,6-dimethyl-1,2-phenylene dibenzoate; 3-isobutyl-4,6-dimethyl-1,2-phenylene dibenzoate; 3-cyclopentyl-4,6-dimethyl-1,2-phenylene dibenzoate; 3-cyclohexyl-4,6-dimethyl-1,2-phenylene dibenzoate; 4,6-dimethylbiphenyl-2,3-diyl dibenzoate; 4-ethyl-3,6-dimethyl-1,2-phenylene dibenzoate; 3,4-diethyl-6-methyl-1,2-phenylene dibenzoate; 4-ethyl-6-methyl-3-propyl-1,2-phenylene dibenzoate; 4-ethyl-3-isopropyl-6-methyl-1,2-phenylene dibenzoate; 3-butyl-4-ethyl-6-methyl-1,2-phenylene dibenzoate; 4-ethyl-3-isobutyl-6-methyl-1,2-phenylene dibenzoate; 3-cyclopentyl-4-ethyl-6-methyl-1,2-phenylene dibenzoate; 3-cyclohexyl-4-ethyl-6-methyl-1,2-phenylene dibenzoate; 6-ethyl-4-methylbiphenyl-2,3-diyl dibenzoate; 3,6-dimethyl-4-propyl-1,2-phenylene dibenzoate; 3-ethyl-6-methyl-4-propyl-1,2-phenylene dibenzoate; 6-methyl-3,4-dipropyl-1,2-phenylene dibenzoate; 3-isopropyl-6-methyl-4-propyl-1,2-phenylene dibenzoate; 3-butyl-6-methyl-4-propyl-1,2-phenylene dibenzoate; 3-isobutyl-6-methyl-4-propyl-1,2-phenylene dibenzoate; 3-cyclopentyl-6-methyl-4-propyl-1,2-phenylene dibenzoate; 3-cyclohexyl-6-methyl-4-propyl-1,2-phenylene dibenzoate; 4-methyl-6-propylbiphenyl-2,3-diyl dibenzoate; 4-isopropyl-3,6-dimethyl-1,2-phenylene dibenzoate; 3-ethyl-4-isopropyl-6-methyl-1,2-phenylene dibenzoate; 4-isopropyl-6-methyl-3-propyl-1,2-phenylene dibenzoate; 3,4-diisopropyl-6-methyl-1,2-phenylene dibenzoate; 3-butyl-4-isopropyl-6-methyl-1,2-phenylene dibenzoate; 3-isobutyl-4-isopropyl-6-methyl-1,2-phenylene dibenzoate; 3-cyclopentyl-4-isopropyl-6-methyl-1,2-phenylene dibenzoate; 3-cyclohexyl-4-isopropyl-6-methyl-1,2-phenylene dibenzoate; 6-isopropyl-4-methylbiphenyl-2,3-diyl dibenzoate; 4-butyl-3,6-dimethyl-1,2-phenylene dibenzoate; 4-butyl-3-ethyl-6-methyl-1,2-phenylene dibenzoate; 4-butyl-6-methyl-3-propyl-1,2-phenylene dibenzoate; 4-butyl-3-isopropyl-6-methyl-1,2-phenylene dibenzoate; 3,4-dibutyl-6-methyl-1,2-phenylene dibenzoate; 4-butyl-3-isobutyl-6-methyl-1,2-phenylene dibenzoate; 4-butyl-3-cyclopentyl-6-methyl-1,2-phenylene dibenzoate; 4-butyl-3-cyclohexyl-6-methyl-1,2-phenylene dibenzoate; 4-butyl-6-methyl-3-(2,4,4-trimethylpentan-2-yl)-1,2-phenylene dibenzoate; 6-butyl-4-methylbiphenyl-2,3-diyl dibenzoate; 4-isobutyl-3,6-dimethyl-1,2-phenylene dibenzoate; 3-ethyl-4-isobutyl-6-methyl-1,2-phenylene dibenzoate; 4-isobutyl-6-methyl-3-propyl-1,2-phenylene dibenzoate; 4-isobutyl-3-isopropyl-6- methyl-1,2-phenylene dibenzoate; 3-butyl-4-isobutyl-6-methyl-1,2-phenylene dibenzoate; 3,4-diisobutyl-6-methyl-1,2-phenylene dibenzoate; 3-cyclopentyl-4-isobutyl-6-methyl-1,2-phenylene dibenzoate; 3-cyclohexyl-4-isobutyl-6-methyl-1,2-phenylene dibenzoate; 6-isobutyl-4-methylbiphenyl-2,3-diyl dibenzoate; 4-tert-butyl-3,6-dimethyl-1,2-phenylene dibenzoate; 4-tert-butyl-3-ethyl-6-methyl-1,2-phenylene dibenzoate; 4-tert-butyl-6-methyl-3-propyl-1,2-phenylene dibenzoate; 4-tert-butyl-3-isopropyl-6-methyl-1,2-phenylene dibenzoate; 4-tert-butyl-3-butyl-6-methyl-1,2-phenylene dibenzoate; 4-tert-butyl-3-isobutyl-6-methyl-1,2-phenylene dibenzoate; 4-tert-butyl-3-cyclopentyl-6-methyl-1,2-phenylene dibenzoate; 4-tert-butyl-3-cyclohexyl-6-methyl-1,2-phenylene dibenzoate; 4-cyclopentyl-3,6-dimethyl-1,2-phenylene dibenzoate; 4-cyclopentyl-3-ethyl-6-methyl-1,2-phenylene dibenzoate; 4-cyclopentyl-6-methyl-3-propyl-1,2-phenylene dibenzoate; 4-cyclopentyl-3-isopropyl-6-methyl-1,2-phenylene dibenzoate; 3-butyl-4-cyclopentyl-6-methyl-1,2-phenylene dibenzoate; 4-cyclopentyl-3-isobutyl-6-methyl-1,2-phenylene dibenzoate; 3,4-dicyclopentyl-6-methyl-1,2-phenylene dibenzoate; 3-cyclohexyl-4-cyclopentyl-6-methyl-1,2-phenylene dibenzoate; 6-cyclopentyl-4-methylbiphenyl-2,3-diyl dibenzoate; 4-cyclohexyl-3,6-dimethyl-1,2-phenylene dibenzoate; 4-cyclohexyl-3-ethyl-6-methyl-1,2-phenylene dibenzoate; 4-cyclohexyl-6-methyl-3-propyl-1,2-phenylene dibenzoate; 4-cyclohexyl-3-isopropyl-6-methyl-1,2-phenylene dibenzoate; 3-butyl-4-cyclohexyl-6-methyl-1,2-phenylene dibenzoate; 4-cyclohexyl-3-isobutyl-6-methyl-1,2-phenylene dibenzoate; 4-cyclohexyl-3-cyclopentyl-6-methyl-1,2-phenylene dibenzoate; 3,4-dicyclohexyl-6-methyl-1,2-phenylene dibenzoate; 6-cyclohexyl-4-methylbiphenyl-2,3-diyl dibenzoate; 2,5-dimethylbiphenyl-3,4-diyl dibenzoate; 2-ethyl-5-methylbiphenyl-3,4-diyl dibenzoate; 5-methyl-2-propylbiphenyl-3,4-diyl dibenzoate; 2-isopropyl-5-methylbiphenyl-3,4-diyl dibenzoate; 2-butyl-5-methylbiphenyl-3,4-diyl dibenzoate; 2-isobutyl-5-methylbiphenyl-3,4-diyl dibenzoate; 2-cyclopentyl-5-methylbiphenyl-3,4-diyl dibenzoate; 2-cyclohexyl-5-methylbiphenyl-3,4-diyl dibenzoate; 3,4-phenyl-6-methyl-1,2-phenylene dibenzoate; 6-ethyl-3,4-dimethyl-1,2-phenylene dibenzoate; 3,6-diethyl-4-methyl-1,2-phenylene dibenzoate; 6-ethyl-4-methyl-3-propyl-1,2-phenylene dibenzoate; 6-ethyl-3-isopropyl-4-methyl-1,2-phenylene dibenzoate; 3-butyl-6-ethyl-4-methyl-1,2-phenylene dibenzoate; 6-ethyl-3-isobutyl-4-methyl-1,2-phenylene dibenzoate; 3-cyclopentyl-6-ethyl-4-methyl-1,2-phenylene dibenzoate; 3-cyclohexyl-6-ethyl-4-methyl-1,2-phenylene dibenzoate; 4-ethyl-6-methylbiphenyl-2,3-diyl dibenzoate; 4,6-diethyl-3-methyl-1,2-phenylene dibenzoate; 3,4,6-triethyl-1,2-phenylene dibenzoate; 4,6-diethyl-3-propyl-1,2-phenylene dibenzoate; 4,6-diethyl-3-isopropyl-1,2-phenylene dibenzoate; 3-butyl-4,6-diethyl-1,2-phenylene dibenzoate; 4,6-diethyl-3-isobutyl-1,2-phenylene dibenzoate; 3-cyclopentyl-4,6-diethyl-1,2-phenylene dibenzoate; 3-cyclohexyl-4,6-diethyl-1,2-phenylene dibenzoate; 4,6-diethylbiphenyl-2,3-diyl dibenzoate; 6-ethyl-3-methyl-4-propyl-1,2-phenylene dibenzoate; 3,6-diethyl-4-propyl-1,2-phenylene dibenzoate; 6-ethyl-3,4-dipropyl-1,2-phenylene dibenzoate; 6-ethyl-3-isopropyl-4-propyl-1,2-phenylene dibenzoate; 3-butyl-6-ethyl-4-propyl-1,2-phenylene dibenzoate; 6-ethyl-3-isobutyl-4-propyl-1,2-phenylene dibenzoate; 3-cyclopentyl-6-ethyl-4-propyl-1,2-phenylene dibenzoate; 3-cyclohexyl-6-ethyl-4-propyl-1,2-phenylene dibenzoate; 4-ethyl-6-propylbiphenyl-2,3-diyl dibenzoate; 6-ethyl-4-isopropyl-3-methyl-1,2-phenylene dibenzoate; 3,6-diethyl-4-isopropyl-1,2-phenylene dibenzoate; 6-ethyl-4-isopropyl-3-propyl-1,2-phenylene dibenzoate; 6-ethyl-3,4-disopropyl-1,2-phenylene dibenzoate; 3-butyl-6-ethyl-4-isopropyl-1,2-phenylene dibenzoate; 6-ethyl-3-isobutyl-4-isopropyl-1,2-phenylene dibenzoate; 3-cyclopentyl-6-ethyl-4-isopropyl-1,2-phenylene dibenzoate; 3-cyclohexyl-6-ethyl-4-isopropyl-1,2-phenylene dibenzoate; 4-ethyl-6-isopropylbiphenyl-2,3-diyl dibenzoate; 4-butyl-6-ethyl-3-methyl-1,2-phenylene dibenzoate; 4-butyl-3,6-diethyl-1,2-phenylene dibenzoate; 4-butyl-6-ethyl-3-propyl-1,2-phenylene dibenzoate; 4-butyl-6-ethyl-3-isopropyl-1,2-phenylene dibenzoate; 3,4-dibutyl-6-ethyl-1,2-phenylene dibenzoate; 4-butyl-6-ethyl-3-isobutyl-1,2-phenylene dibenzoate; 4-butyl-3-cyclopentyl-6-ethyl-1,2-phenylene dibenzoate; 4-butyl-3-cyclohexyl-6-ethyl-1,2-phenylene dibenzoate; 6-butyl-4-ethylbiphenyl-2,3-diyl dibenzoate; 6-ethyl-4-isobutyl-3-methyl-1,2-phenylene dibenzoate; 3,6-diethyl-4-isobutyl-1,2-phenylene dibenzoate; 6-ethyl-4-isobutyl-3-propyl-1,2-phenylene dibenzoate; 6-ethyl-4-isobutyl-3-isopropyl-1,2-phenylene dibenzoate; 3-butyl-6-ethyl-4-isobutyl-1,2-phenylene dibenzoate; 6-ethyl-3,4-diisobutyl-1,2-phenylene dibenzoate; 3-cyclopentyl-6-ethyl-4-isobutyl-1,2-phenylene dibenzoate; 3-cyclohexyl-6-ethyl-4-isobutyl-1,2-phenylene dibenzoate; 4-ethyl-6-isobutylbiphenyl-2,3-diyl dibenzoate; 4-tert-butyl-6-ethyl-3-methyl-1,2-phenylene dibenzoate; 4-tert-butyl-3,6-diethyl-1,2-phenylene dibenzoate; 4-tert-butyl-6-ethyl-3-propyl-1,2-phenylene dibenzoate; 4-tert-butyl-6-ethyl-3-isopropyl-1,2-phenylene dibenzoate; 4-tert-butyl-3-butyl-6-ethyl-1,2-phenylene dibenzoate; 4-tert-butyl-6-ethyl-3-isobutyl-1,2-phenylene dibenzoate; 4-tert-butyl-3-cyclopentyl-6-ethyl-1,2-phenylene dibenzoate; 4-tert-butyl-3-cyclohexyl-6-ethyl-1,2-phenylene dibenzoate; 4-cyclopentyl-6-ethyl-3-methyl-1,2-phenylene dibenzoate; 4-cyclopentyl-3,6-diethyl-1,2-phenylene dibenzoate; 4-cyclopentyl-6-ethyl-3-propyl-1,2-phenylene dibenzoate; 4-cyclopentyl-6-ethyl-3-isopropyl-1,2-phenylene dibenzoate; 3-butyl-4-cyclopentyl-6-ethyl-1,2-phenylene dibenzoate; 4-cyclopentyl-6-ethyl-3-isobutyl-1,2-phenylene dibenzoate; 3,4-dicyclopentyl-6-ethyl-1,2-phenylene dibenzoate; 3-cyclohexyl-4-cyclopentyl-6-ethyl-1,2-phenylene dibenzoate; 6-cyclopentyl-4-ethylbiphenyl-2,3-diyl dibenzoate; 4-cyclohexyl-6-ethyl-3-methyl-1,2-phenylene dibenzoate; 4-cyclohexyl-3,6-diethyl-1,2-phenylene dibenzoate; 4-cyclohexyl-6-ethyl-3-propyl-1,2-phenylene dibenzoate; 4-cyclohexyl-6-ethyl-3-isopropyl-1,2-phenylene dibenzoate; 3-butyl-4-cyclohexyl-6-ethyl-1,2-phenylene dibenzoate; 4-cyclohexyl-6-ethyl-3-isobutyl-1,2-phenylene dibenzoate; 4-cyclohexyl-3-cyclopentyl-6-ethyl-1,2-phenylene dibenzoate; 3,4-dicyclohexyl-6-ethyl-1,2-phenylene dibenzoate; 6-cyclohexyl-4-ethylbiphenyl-2,3-diyl dibenzoate; 5-ethyl-2-methylbiphenyl-3,4-diyl dibenzoate; 2,5-diethylbiphenyl-3,4-diyl dibenzoate; 5-ethyl-2-propylbiphenyl-3,4-diyl dibenzoate; 5-ethyl-2-isopropylbiphenyl-3,4-diyl dibenzoate; 2-butyl-5-ethylbiphenyl-3,4-diyl dibenzoate; 5-ethyl-2-isobutylbiphenyl-3,4-diyl dibenzoate; 2-cyclopentyl-5-ethylbiphenyl-3,4-diyl dibenzoate; 2-cyclohexyl-5-ethylbiphenyl-3,4-diyl dibenzoate, 5-ethyl-2-(2,4,4-trimethylpentan-2-yl)biphenyl-3,4-diyl dibenzoate; 3,4-diphenyl-6-ethyl-1,2-phenylene dibenzoate; 3,4-dimethyl-6-propyl-1,2-phenylene dibenzoate; 3-ethyl-4-methyl-6-propyl-1,2-phenylene dibenzoate; 4-methyl-3,6-dipropyl-1,2-phenylene dibenzoate; 3-isopropyl-4-methyl-6-propyl-1,2-phenylene dibenzoate; 3-butyl-4-methyl-6-propyl-1,2-phenylene dibenzoate; 3-isobutyl-4-methyl-6-propyl-1,2-phenylene dibenzoate; 3-cyclopentyl-4-methyl-6-propyl-1,2-phenylene dibenzoate; 3-cyclohexyl-4-methyl-6-propyl-1,2-phenylene dibenzoate; 6-methyl-4-propylbiphenyl-2,3-diyl dibenzoate; 4-ethyl-3-methyl-6-propyl-1,2-phenylene dibenzoate; 3,4-diethyl-6-propyl-1,2-phenylene dibenzoate; 4-ethyl-3,6-dipropyl-1,2-phenylene dibenzoate; 4-ethyl-3-isopropyl-6-propyl-1,2-phenylene dibenzoate; 3-butyl-4-ethyl-6-propyl-1,2-phenylene dibenzoate; 4-ethyl-3-isobutyl-6-propyl-1,2-phenylene dibenzoate; 3-cyclopentyl-4-ethyl-6-propyl-1,2-phenylene dibenzoate; 3-cyclohexyl-4-ethyl-6-propyl-1,2-phenylene dibenzoate; 6-ethyl-4-propylbiphenyl-2,3-diyl dibenzoate; 3-methyl-4,6-dipropyl-1,2-phenylene dibenzoate; 3-ethyl-4,6-dipropyl-1,2-phenylene dibenzoate; 3,4,6-tripropyl-1,2-phenylene dibenzoate; 3-isopropyl-4,6-dipropyl-1,2-phenylene dibenzoate; 3-butyl-4,6-dipropyl-1,2-phenylene dibenzoate; 3-isobutyl-4,6-dipropyl-1,2-phenylene dibenzoate; 3-cyclopentyl-4,6-dipropyl-1,2-phenylene dibenzoate; 3-cyclohexyl-4,6-dipropyl-1,2-phenylene dibenzoate; 4,6-dipropyl-biphenyl-2,3-diyl dibenzoate; 4-isopropyl-3-methyl-6-propyl-1,2-phenylene dibenzoate; 3-ethyl-4-isopropyl-6-propyl-1,2-phenylene dibenzoate; 4-isopropyl-3,6-dipropyl-1,2-phenylene dibenzoate; 3,4-diisopropyl-6-propyl-1,2-phenylene dibenzoate; 3-butyl-4-isopropyl-6-propyl-1,2-phenylene dibenzoate; 3-isobutyl-4-isopropyl-6-propyl-1,2-phenylene dibenzoate; 3-cyclopentyl-4-isopropyl-6-propyl-1,2-phenylene dibenzoate; 3-cyclohexyl-4-isopropyl-6-propyl-1,2-phenylene dibenzoate; 6-isopropyl-4-propylbiphenyl-2,3-diyl dibenzoate; 4-butyl-3-methyl-6-propyl-1,2-phenylene dibenzoate; 4-butyl-3-ethyl-6-propyl-1,2-phenylene dibenzoate; 4-butyl-3,6-dipropyl-1,2-phenylene dibenzoate; 4-butyl-3-isopropyl-6-propyl-1,2-phenylene dibenzoate; 3,4-dibutyl-6-propyl-1,2-phenylene dibenzoate; 4-butyl-3-isobutyl-6-propyl-1,2-phenylene dibenzoate; 4-butyl-3-cyclopentyl-6-propyl-1,2-phenylene dibenzoate; 4-butyl-3-cyclohexyl-6-propyl-1,2-phenylene dibenzoate; 6-butyl-4-propylbiphenyl-2,3-diyl dibenzoate; 4-isobutyl-3-methyl-6-propyl-1,2-phenylene dibenzoate; 3-ethyl-4-isobutyl-6-propyl-1,2-phenylene dibenzoate; 4-isobutyl-3,6-dipropyl-1,2-phenylene dibenzoate; 4-isobutyl-3-isopropyl-6-propyl-1,2-phenylene dibenzoate; 3-butyl-4-isobutyl-6-propyl-1,2-phenylene dibenzoate; 3,4-diisobutyl-6-propyl-1,2-phenylene dibenzoate; 3-cyclopentyl-4-isobutyl-6-propyl-1,2-phenylene dibenzoate; 3-cyclohexyl-4-isobutyl-6-propyl-1,2-phenylene dibenzoate; 6-isobutyl-4-propylbiphenyl-2,3-diyl dibenzoate; 4-tert-butyl-3-methyl-6-propyl-1,2-phenylene dibenzoate; 4-tert-butyl-3-ethyl-6-propyl-1,2-phenylene dibenzoate; 4-tert-butyl-3,6-dipropyl-1,2-phenylene dibenzoate; 4-tert-butyl-3-isopropyl-6-propyl-1,2-phenylene dibenzoate; 4-tert-butyl-3-butyl-6-propyl-1,2-phenylene dibenzoate; 4-tert-butyl-3-isobutyl-6-propyl-1,2-phenylene dibenzoate; 4-tert-butyl-3-cyclopentyl-6-propyl-1,2-phenylene dibenzoate; 4-tert-butyl-3-cyclohexyl-6-propyl-1,2-phenylene dibenzoate; 4-cyclopentyl-3-methyl-6-propyl-1,2-phenylene dibenzoate; 4-cyclopentyl-3-ethyl-6-propyl-1,2-phenylene dibenzoate; 4-cyclopentyl-3,6-dipropyl-1,2-phenylene dibenzoate; 4-cyclopentyl-3-isopropyl-6-propyl-1,2-phenylene dibenzoate; 3-butyl-4-cyclopentyl-6-propyl-1,2-phenylene dibenzoate; 4-cyclopentyl-3-isobutyl-6-propyl-1,2-phenylene dibenzoate; 3,4-dicyclopentyl-6-propyl-1,2-phenylene dibenzoate; 3-cyclohexyl-4-cyclopentyl-6-propyl-1,2-phenylene dibenzoate; 6-cyclopentyl-4-propylbiphenyl-2,3-diyl dibenzoate; 4-cyclohexyl-3-methyl-6-propyl-1,2-phenylene dibenzoate; 4-cyclohexyl-3-ethyl-6-propyl-1,2-phenylene dibenzoate; 4-cyclohexyl-3,6-dipropyl-1,2-phenylene dibenzoate; 4-cyclohexyl-3-isopropyl-6-propyl-1,2-phenylene dibenzoate; 3-butyl-4-cyclohexyl-6-propyl-1,2-phenylene dibenzoate; 4-cyclohexyl-3-isobutyl-6-propyl-1,2-phenylene dibenzoate; 4-cyclohexyl-3-cyclopentyl-6-propyl-1,2-phenylene dibenzoate; 3,4-dicyclohexyl-6-propyl-1,2-phenylene dibenzoate; 6-cyclohexyl-4-propylbiphenyl-2,3-diyl dibenzoate; 2-methyl-5-propylbiphenyl-3,4-diyl dibenzoate; 2-ethyl-5-propylbiphenyl-3,4-diyl dibenzoate; 2,5-dipropylbiphenyl-3,4-diyl dibenzoate; 2-isopropyl-5-propylbiphenyl-3,4-diyl dibenzoate; 2-butyl-5-propylbiphenyl-3,4-diyl dibenzoate; 2-isobutyl-5-propylbiphenyl-3,4-diyl dibenzoate; 2-cyclopentyl-5-propylbiphenyl-3,4-diyl dibenzoate; 2-cyclohexyl-5-propylbiphenyl-3,4-diyl dibenzoate; and/or 3,4-diphenyl-6-propyl-1,2-phenylene dibenzoate.

Another composition is provided. In an embodiment, a substituted phenylene aromatic diester of the structure (II) is provided:

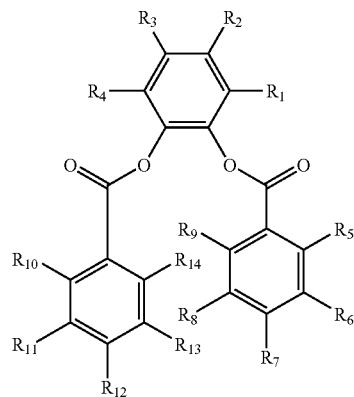

wherein $R_1$-$R_{14}$ are the same or different. Each of $R_1$-$R_{14}$ is selected from hydrogen, an unsubstituted hydrocarbyl group having 1 to 20 carbon atoms, a halohydrocarbyl group, a halogen, a silicon-containing hydrocarbyl group, and combinations thereof. At least one of $R_5$-$R_9$ is different than its respective $R_{10}$-$R_{14}$ mate.

In an embodiment, at least one of $R_1$-$R_4$ is substituted and is selected from an unsubstituted hydrocarbyl group having 1 to 20 carbon atoms, a substituted hydrocarbyl group having 1 to 20 atoms, and a halogen.

Another composition is provided. In an embodiment, a substituted phenylene aromatic diester is provided with the structure (IV) below.

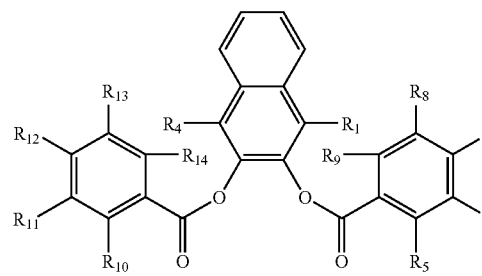

$R_{5-14}$ are the same or different. Each of $R_1$, $R_4$ and $R_5$-$R_{14}$ is selected from hydrogen, an unsubstituted hydrocarbyl group having 1 to 20 carbon atoms, a substituted hydrocarbyl having 1 to 20 atoms, a halohydrocarbyl group, a halogen, a silicon-containing hydrocarbyl group, and combinations thereof.

In an embodiment, any R group of $R_1$, $R_4$ and $R_{5-14}$ that is not hydrogen is an unsubstituted hydrocarbyl group. In a further embodiment, the hydrocarbyl group is an alkyl group.

In an embodiment, each of $R_1$ and $R_4$ is hydrogen. $R_{5-14}$ are the same or different. At least one of $R_5$-$R_{14}$ is selected from an unsubstituted hydrocarbyl group having 1 to 20 carbon atoms, a halohydrocarbyl group, a halogen, a silicon-containing hydrocarbyl group, and combinations thereof. $R_7$ and $R_{12}$ are not simultaneously a methyl group. In other words, $R_7$ is not a methyl group when $R_{12}$ is a methyl group (and vice versa).

The 2,3-naphthalene moiety may or may not be substituted. In one embodiment, the 2,3-naphthalene moiety may be substituted with one or more $C_2$-$C_{20}$ alkyl groups or more than 2 methyl groups. In another embodiment, the 2,3-naphthalene moiety is unsubstituted (i.e., $R_1$ and $R_4$ are hydrogen).

In an embodiment, each R group of $R_5$-$R_{14}$ is a non-cyclic structure.

Any of the compositions disclosed herein may include two or more embodiments disclosed herein.

Any of the compositions disclosed herein may be made by one or more processes disclosed herein.

In an embodiment, one, some, or all of the foregoing compositions include no substituent that contains an active hydrogen. Nonlimiting examples of substituents with an active hydrogen include a hydroxyl group and a carboxylic acid group. Not wishing to be bound by any particular theory, it is believed that the active hydrogen(s) may react with $TiCl_4$ and/or other catalyst components during catalyst synthesis and impair the performance of the resultant catalyst. It is also preferred to minimize the number of electron donating groups in the $R_1$-$R_{14}$ substituents. It is believed that extra electron donating group(s) may poison catalyst active sites.

The present compositions may comprise two or more embodiments disclosed herein.

The present substituted phenylene aromatic diester(s) may be used in procatalyst compositions and/or catalyst compositions for the polymerization of olefin-based polymers. For example, the present substituted phenylene aromatic diester(s) may be used as an internal electron donor and/or an external electron donor in a Ziegler-Natta catalyst system. Provision of the present substituted phenylene aromatic diester(s) in catalyst systems advantageously enhances catalyst stereoselectivity and catalyst activity. Catalyst systems which include the present substituted phenylene aromatic diester(s) advantageously produce olefin-based polymers (and propylene-based polymers in particular) with broad molecular weight distribution and high catalyst activity.

Any of the substituted phenylene aromatic diesters disclosed herein may be a component of a procatalyst composition and/or a catalyst composition as disclosed in U.S. Patent Application No. 61/141,902 filed on Dec. 31, 2008, the entire content of which is incorporated by reference herein.

DEFINITIONS

All references to the Periodic Table of the Elements herein shall refer to the Periodic Table of the Elements, published and copyrighted by CRC Press, Inc., 2003. Also, any references to a Group or Groups shall be to the Groups or Groups reflected in this Periodic Table of the Elements using the IUPAC system for numbering groups. Unless stated to the contrary, implicit from the context, or customary in the art, all parts and percents are based on weight. For purposes of United States patent practice, the contents of any patent, patent application, or publication referenced herein are hereby incorporated by reference in their entirety (or the equivalent US version thereof is so incorporated by reference), especially with respect to the disclosure of synthetic techniques, definitions (to the extent not inconsistent with any definitions provided herein) and general knowledge in the art.

The term "comprising," and derivatives thereof, is not intended to exclude the presence of any additional component, step or procedure, whether or not the same is disclosed herein. In order to avoid any doubt, all compositions claimed herein through use of the term "comprising" may include any additional additive, adjuvant, or compound whether polymeric or otherwise, unless stated to the contrary. In contrast, the term, "consisting essentially of" excludes from the scope of any succeeding recitation any other component, step or procedure, excepting those that are not essential to operability. The term "consisting of" excludes any component, step or procedure not specifically delineated or listed. The term "or", unless stated otherwise, refers to the listed members individually as well as in any combination.

Any numerical range recited herein, includes all values from the lower value to the upper value, in increments of one unit, provided that there is a separation of at least 2 units between any lower value and any higher value. As an example, if it is stated that the amount of a component, or a value of a compositional or a physical property, such as, for example, amount of a blend component, softening temperature, melt index, etc., is between 1 and 100, it is intended that all individual values, such as, 1, 2, 3, etc., and all subranges, such as, 1 to 20, 55 to 70, 197 to 100, etc., are expressly enumerated in this specification. For values which are less than one, one unit is considered to be 0.0001, 0.001, 0.01 or 0.1, as appropriate. These are only examples of what is specifically intended, and all possible combinations of numerical values between the lowest value and the highest value enumerated, are to be considered to be expressly stated in this application. In other words, any numerical range recited herein includes any value or subrange within the stated range. Numerical ranges have been recited, as discussed herein, reference melt index, melt flow rate, and other properties.

The terms "blend" or "polymer blend," as used herein, is a blend of two or more polymers. Such a blend may or may not be miscible (not phase separated at molecular level). Such a blend may or may not be phase separated. Such a blend may or may not contain one or more domain configurations, as determined from transmission electron spectroscopy, light scattering, x-ray scattering, and other methods known in the art.

The term "composition," as used herein, includes a mixture of materials which comprise the composition, as well as reaction products and decomposition products formed from the materials of the composition.

The term "polymer" is a macromolecular compound prepared by polymerizing monomers of the same or different type. "Polymer" includes homopolymers, copolymers, terpolymers, interpolymers, and so on. The term "interpolymer" means a polymer prepared by the polymerization of at least two types of monomers or comonomers. It includes, but is not limited to, copolymers (which usually refers to polymers prepared from two different types of monomers or comonomers, terpolymers (which usually refers to polymers prepared from three different types of monomers or comonomers), tetrapolymers (which usually refers to polymers prepared from four different types of monomers or comonomers), and the like.

The term "olefin-based polymer" is a polymer containing, in polymerized form, a majority weight percent of an olefin, for example ethylene or propylene, based on the total weight of the polymer. Nonlimiting examples of olefin-based polymers include ethylene-based polymers and propylene-based polymers.

The term, "propylene-based polymer," as used herein, refers to a polymer that comprises a majority weight percent polymerized propylene monomer (based on the total amount of polymerizable monomers), and optionally may comprise at least one polymerized comonomer.

The term "alkyl," as used herein, refers to a branched or unbranched, saturated or unsaturated acyclic hydrocarbon radical. Nonlimiting examples of suitable alkyl radicals include, for example, methyl, ethyl, n-propyl, i-propyl, 2-propenyl (or allyl), vinyl, n-butyl, t-butyl, i-butyl (or 2-methylpropyl), etc. The alkyls have 1 and 20 carbon atoms.

The term "substituted alkyl," as used herein, refers to an alkyl as just described in which one or more hydrogen atom bound to any carbon of the alkyl is replaced by another group such as a halogen, aryl, substituted aryl, cycloalkyl, substituted cycloalkyl, heterocycloalkyl, substituted heterocycloalkyl, halogen, haloalkyl, hydroxy, amino, phosphido, alkoxy, amino, thio, nitro, and combinations thereof. Suitable substituted alkyls include, for example, benzyl, trifluoromethyl and the like.

The term "aryl," as used herein, refers to an aromatic substituent which may be a single aromatic ring or multiple aromatic rings which are fused together, linked covalently, or linked to a common group such as a methylene or ethylene moiety. The aromatic ring(s) may include phenyl, naphthyl, anthracenyl, and biphenyl, among others. The aryls have 1 and 20 carbon atoms.

By way of example and not by limitation, examples of the present disclosure will now be provided.

1. Synthesis of 1,2-Phenylene Aromatic Diester.

Method A: A 250-ml round-bottom flask is charged with catechol (0.025 mol), pyridine (0.05 mol, 1.0 equiv.), and dichloromethane (50 ml). The flask is cooled in an ice-water bath, and acyl chloride (0.05 mol, 1.0 equiv.) is added dropwise. Upon completion of addition, the reaction mixture is warmed up to room temperature and stirred overnight. The mixture is diluted with additional dichloromethane, and washed with saturated NH$_4$Cl/1N HCl, water, saturated sodium bicarbonate, and brine consequently. The organic layer is collected and dried over magnesium sulfate. After filtration, the filtrate is concentrated, and the residue is dried in vacuo. Most of the crude products are pure enough, which can also be further purified by recrystallization from ethanol (for solid) or by distillation in vacuo to yield the product as white to yellow solid/liquid.

Method B: To 250-ml round-bottom flask was charged with catechol (68.0 mmol, 1.0 equiv.), pyridine (0.14 mol, 2.0 equiv.) and 50 ml of methylene chloride. The flask is cooled to 0° C. in ice-water bath, and acyl chloride (0.14 mol, 2.0 equiv.) is added dropwise. The reaction mixture is stirred overnight at room temperature. The solvent is removed under vacuum residue is dissolved in 200 ml of ether, and filtered to remove solid. The filtrate is washed successively with 100 ml of 0.1 N HCl, water and brine, dried over Na$_2$SO$_4$. After filtration, the filtrate is concentrated to give the crude product, which is purified by recrystallization in ethanol to yield final product.

Method C: A 250-ml round-bottom flask is charged with 4-tert-butylbenzene-1,2-diol (0.03 mol), benzyl chloride (0.066 mol, 2.2 equiv.), bismuth triflate (1.05 mmol, 0.035 equiv.) and dichloromethane (100 ml). The reaction mixture is stirred overnight at room temperature. The solvent is removed via evaporation under vacuum. The residue is dissolved with ethyl acetate, and washed with aqueous K$_2$CO$_3$, water, and brine consequently. The organic layer is collected and dried over sodium sulfate. After filtration, the filtrate is concentrated. The crude product is purified by recrystallization from ethyl ether and hexanes.

Method D: A 250-ml round-bottom flask is charged with 5-tert-butyl-3-methylbenzene-1,2-diol (0.02 mol), acyl chloride (0.044 mol, 2.2 equiv.), bismuth triflate (0.7 mmol, 0.035 equiv.) and dichloromethane (100 ml). The reaction mixture is stirred overnight at room temperature. The solvent is removed via evaporation under vacuum. The residue is dissolved with ethyl acetate, and washed with aqueous K$_2$CO$_3$, water, and brine consequently. The organic layer is collected and dried over sodium sulfate. After filtration, the filtrate is concentrated. The crude product is purified by recrystallization from ethyl ether and hexanes.

Nonlimiting examples of compounds produced by way of the foregoing synthesis are provided in Table 1 below.

TABLE 1

| Compound | Synthesis Method | Structure | $^1$H NMR (500 MHz, CDCl3, ppm) |
|---|---|---|---|
| 1,2-phenylene dibenzoate | A | 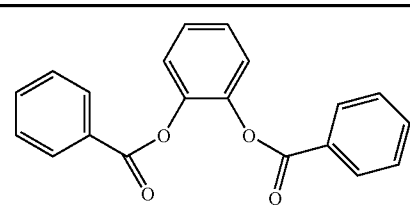 | 8.08 (dd, 4H), 7.54 (tt, 2H), 7.34-7.43 (m, 8H). |
| 3-methyl-5-tert-butyl-1,2-phenylene dibenzoate | A | 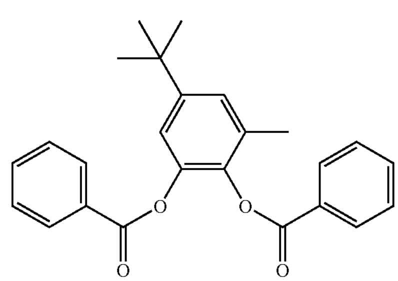 [SMILES: Cc1cc(C(C)(C)C)cc(OC(=O)c2ccccc2)c1OC(=O)c1ccccc1] | 8.08 (dd, 2H), 8.03 (dd, 2H), 7.53 (tt, 1H), 7.50 (tt, 1H), 7.38 (t, 2H), 7.34 (t, 2H), 7.21 (d, 1H), 7.19 (d, 1H), 2.28 (s, 3H), 1.34 (s, 9H). |

TABLE 1-continued

| Compound | Synthesis Method | Structure | $^1$H NMR (500 MHz, CDCl3, ppm) |
|---|---|---|---|
| 3-tert-butyl-5-methyl-1,2-phenylene dibenzoate | A | 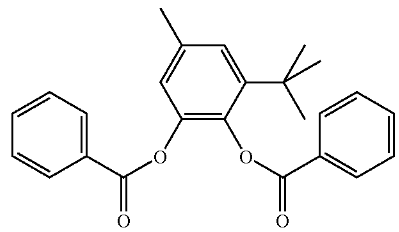 [SMILES: Cc1cc(OC(=O)c2ccccc2)c(OC(=O)c2ccccc2)c(C(C)(C)C)c1] | 8.08 (dd, 2H), 7.93 (dd, 2H), 7.53 (tt, 1H), 7.43 (tt, 1H), 7.38 (t, 2H), 7.25 (t, 2H), 7.16 (d, 1H), 7.11 (d, 1H), 2.41 (s, 3H), 1.38 (s, 9H). |
| 3,5-di-tert-butyl-1,2-phenylene dibenzoate | A | 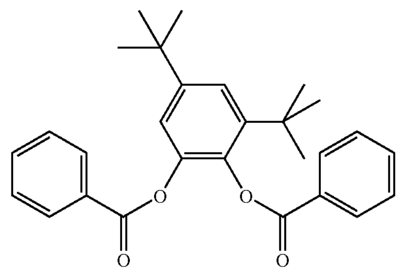 [SMILES: CC(C)(C)c1cc(OC(=O)c2ccccc2)c(OC(=O)c2ccccc2)c(C(C)(C)C)c1] | 8.08 (dd, 2H), 7.94 (dd, 2H), 7.52 (tt, 1H), 7.44 (tt, 1H), 7.36-7.40 (m, 3H), 7.23-7.27 (m, 3H), 1.40 (s, 9H), 1.38 (s, 9H). |
| 3,5-diisoproppyl-1,2-phenylene dibenzoate | A | 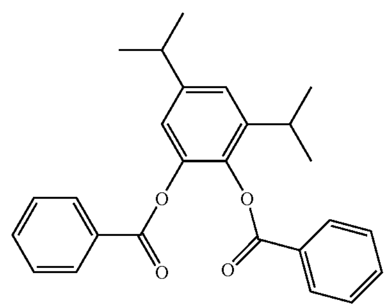 [SMILES: CC(C)c1cc(OC(=O)c2ccccc2)c(OC(=O)c2ccccc2)c(C(C)C)c1] | 8.08 (dd, 2H), 7.00 (dd, 2H), 7.53 (tt, 1H), 7.48 (tt, 1H), 7.39 (t, 2H), 7.31 (t, 2H), 7.11 (d, 1H), 7.09 (d, 1H), 3.11 (heptat, 1H), 2.96 (heptat, 1H), 1.30 (d, 6H), 1.26 (d, 6H). |
| 3,6-dimethyl-1,2-phenylene dibenzoate | A | 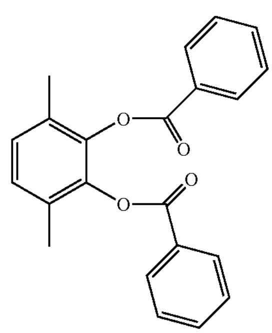 [SMILES: Cc1ccc(C)c(OC(=O)c2ccccc2)c1OC(=O)c1ccccc1] | 8.08 (d, 2H), 7.51 (t, 1H), 7.34 (d, 2H), 7.11 (s, 2H), 2.23 (s, 6H). |
| 4-t-butyl-1,2-phenylene dibenzoate | C | 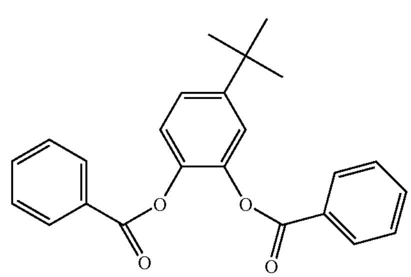 [SMILES: CC(C)(C)c1ccc(OC(=O)c2ccccc2)c(OC(=O)c2ccccc2)c1] | 8.07 (dd, 4H), 7.54 (m, 2H), 7.30-7.40 (m, 7H), 1.37 (s, 9H). |

TABLE 1-continued

| Compound | Synthesis Method | Structure | $^1$H NMR (500 MHz, CDCl3, ppm) |
|---|---|---|---|
| 4-methyl 1,2-phenylene dibenzoate | B | 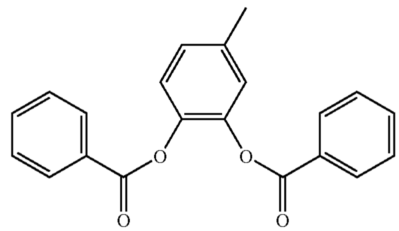 [SMILES: Cc1ccc(OC(=O)c2ccccc2)c(OC(=O)c2ccccc2)c1] | 8.07 (d, 4H), 7.54 (t, 2H), 7.37 (t, 4H), 7.27 (d, 1H), 7.21 (s, 1H), 7.15 (d, 1H), 2.42 (s, 3H). |
| 1,2-naphthalene dibenzoate | A | 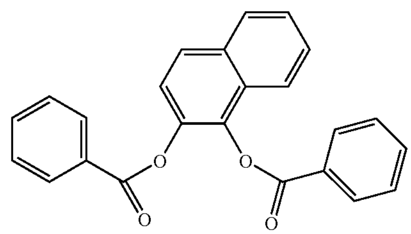 [SMILES: O=C(Oc1ccc2ccccc2c1OC(=O)c1ccccc1)c1ccccc1] | 8.21-8.24 (m, 2H), 8.08-8.12 (m, 2H), 7.90-7.96 (m, 2H), 7.86 (d, 1H), 7.60 (m, 1H), 7.50-7.55 (m, 4H), 7.46 (t, 2H), 7.37 (t, 2H). |
| 2,3-naphthalene dibenzoate | A | 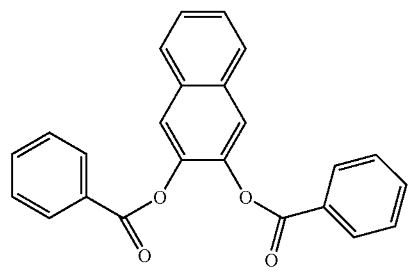 [SMILES: O=C(Oc1cc2ccccc2cc1OC(=O)c1ccccc1)c1ccccc1] | 8.08-8.12 (m, 4H), 7.86-7.90 (m, 4H), 7.51-7.58 (m, 4H), 7.38 (t, 4H) |
| 3-methyl-5-tert-butyl-1,2-phenylene di(4-methylbenzoate) | B | 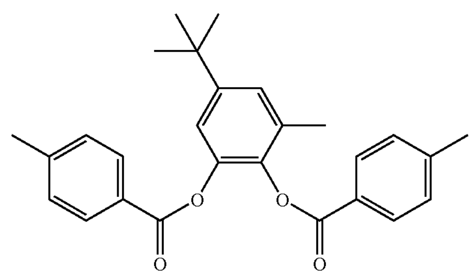 | 7.98 (d, 2H), 7.93 (d, 2H), 7.18 (d, 4H), 7.15 (d, 2H), 2.38 (s, 3H), 2.36 (s, 3H), 2.26 (s, 3H), 1.35 (s, 9H). |
| 3-methyl-5-tert-butyl-1,2-phenylene di(2,4,6-trimethylbenzoate) | B | 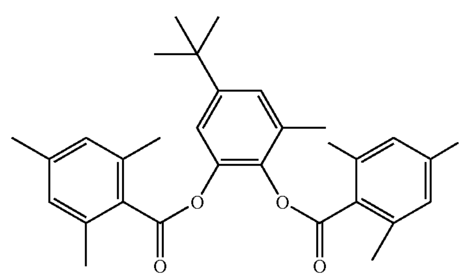 | 7.25 (s, 1H), 7.21 (s, 1H), 6.81 (d, 4H), 2.36 (s, 3H), 2.30 (d, 6H), 2.25 (s, 6H), 2.23 (s, 6H), 1.36 (s, 9H). |
| 3-methyl-5-tert-butyl-1,2-phenylene di(4-fluorobenzoate) | D | 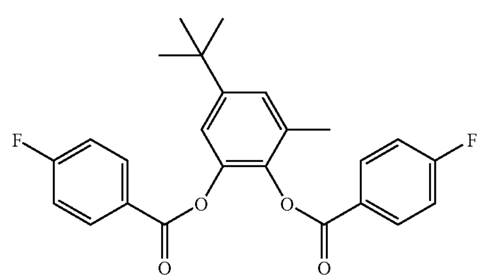 [SMILES: Cc1cc(C(C)(C)C)cc(OC(=O)c2ccc(F)cc2)c1OC(=O)c1ccc(F)cc1] | δ 8.07 (m, 4H), 7.21 (s, 1H), 7.17 (s, 1H), 7.04 (m, 4H), 2.27 (s, 3H), 1.34 (s, 9H) |

TABLE 1-continued

| Compound | Synthesis Method | Structure | ¹H NMR (500 MHz, CDCl3, ppm) |
|---|---|---|---|
| 3,6-dichloro-1,2-phenylene dibenzoate | | 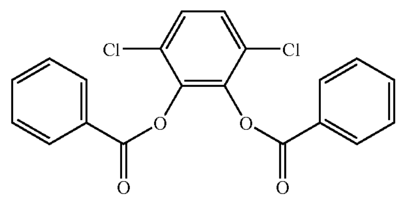 [SMILES: O=C(Oc1c(Cl)ccc(Cl)c1OC(=O)c1ccccc1)c1ccccc1] | 8.10 (d, 2H), 7.57 (t, 1H), 7.41 (d, 2H), 7.49 (s, 2H). |
| 3-methyl-5-tert-butyl-1,2-phenylene di(4-chlorobenzoate) (IED12) | D | 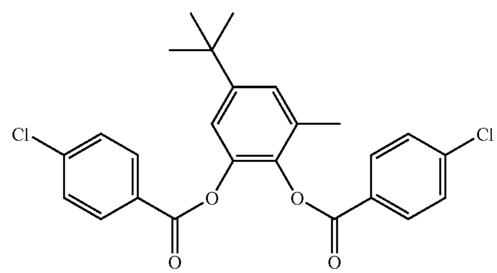 [SMILES: Cc1cc(C(C)(C)C)cc(OC(=O)c2ccc(Cl)cc2)c1OC(=O)c1ccc(Cl)cc1] | 7.98 (dd, 4H), 7.36 (dd, 4H), 7.21 (s, 1H), 7.17 (s, 1H), 2.26 (s, 3H), 1.34 (s, 9H). |
| 3-methyl-5-tert-butyl-1,2-phenylene di(1-naphthoate) | B | 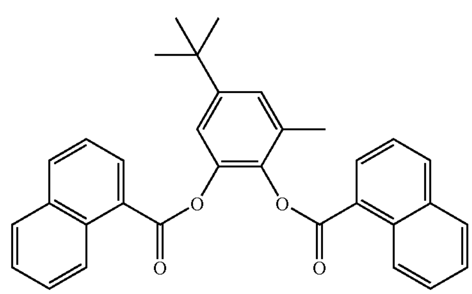 [SMILES: Cc1cc(C(C)(C)C)cc(OC(=O)c2cccc3ccccc23)c1OC(=O)c1cccc2ccccc12] | |
| 3-methyl-5-tert-butyl-1,2-phenylene di(2-naphthoate) | B | 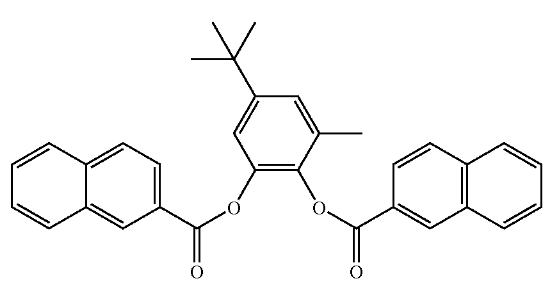 [SMILES: Cc1cc(C(C)(C)C)cc(OC(=O)c2ccc3ccccc3c2)c1OC(=O)c1ccc2ccccc2c1] | |
| 3-methyl-5-tert-butyl-1,2-phenylene di(4-ethoxybenzoate) | B | 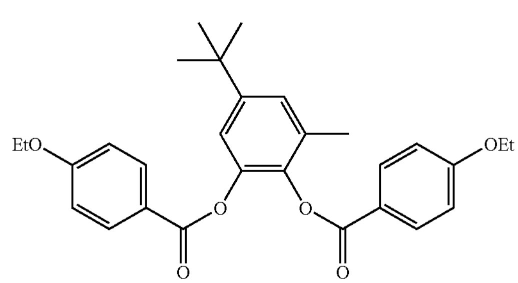 [SMILES: CCOc1ccc(C(=O)Oc2cc(C(C)(C)C)cc(C)c2OC(=O)c2ccc(OCC)cc2)cc1] | δ 8.02 (d, 2H), 7.97 (d, 2H), 7.17 (m, 2H), 6.83 (d, 2H), 6.79 (d, 2H), 4.04 (m, 4H), 2.25 (s, 3H), 1.41 (m, 6H), 1.33 (s, 9H) |

TABLE 1-continued

| Compound | Synthesis Method | Structure | $^1$H NMR (500 MHz, CDCl3, ppm) |
|---|---|---|---|
| 3-methyl-5-(2,4,4-trimethylpentan-2-yl)-1,2-phenylene dibenzoate | B | 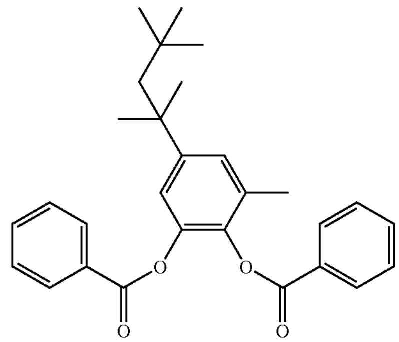 [SMILES: Cc1cc(C(C)(C)CC(C)(C)C)cc(OC(=O)c2ccccc2)c1OC(=O)c1ccccc1] | δ 8.09 (d, 2H), 8.03 (d, 2H), 7.50 (m, 2H), 7.38 (t, 2H), 7.33 (t, 2H), 7.19 (s, 2H), 2.27 (s, 3H), 1.75 (s, 2H), 1.40 (s, 6H), 0.81 (s, 9H) |
| 3-fluoro-1,2-phenylene dibenzoate | D | 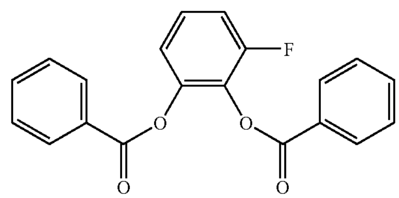 [SMILES: O=C(Oc1cccc(F)c1OC(=O)c1ccccc1)c1ccccc1] | δ 8.10 (d, 2H), 8.07 (d, 2H), 7.56 (m, 2H), 7.40 (m, 4H), 7.31 (m, 1H), 7.18 (m, 2H) |
| 4-tert-butyl-1,2-phenylene di(2-methylbenzoate) | D | 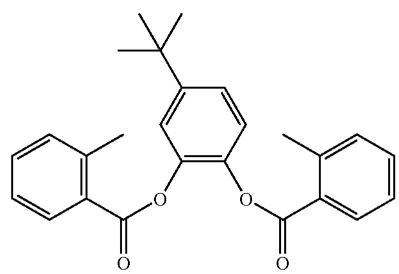 [SMILES: Cc1ccccc1C(=O)Oc1ccc(C(C)(C)C)cc1OC(=O)c1ccccc1C] | δ 8.04 (d, 1H), 8.00 (d, 1H), 7.39 (m, 3H), 7.34 (m, 1H), 7.28 (d, 1H), 7.22 (m, 2H), 7.17 (m, 2H), 2.57 (s, 6H), 1.36 (s, 9H) |
| 4-methyl-1,2-phenylene di(2-methylbenzoate) | D | 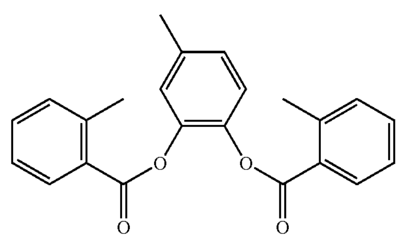 [SMILES: Cc1ccc(OC(=O)c2ccccc2C)c(OC(=O)c2ccccc2C)c1] | δ 8.01 (d, 2H), 7.39 (m, 2H), 7.22 (m, 3H), 7.15 (m, 4H), 2.57 (s, 3H), 2.56 (s, 3H), 2.42 (s, 3H) |
| 4-tert-butyl-1,2-phenylene di(2,4,6-trimethylbenzoate) | D | 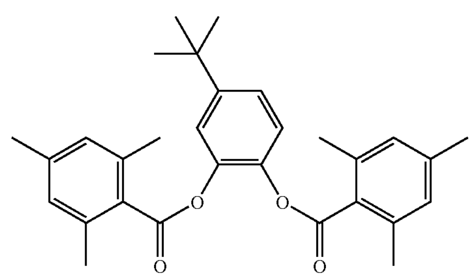 | δ 7.36 (s, 3H), 6.83 (s, 4H), 2.29 (s, 6H), 2.26 (s, 12H), 1.34 (s, 9H) |
| 4-methyl-1,2-phenylene di(2,4,6-trimethylbenzoate) | D | 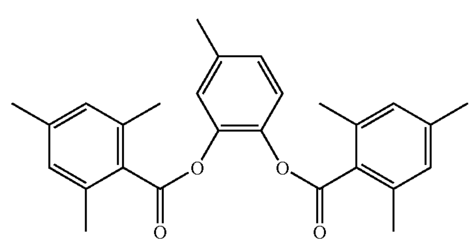 | δ 7.29 (d, 1H), 7.22 (m, 1H), 7.14 (m, 1H), 6.83 (m, 3H), 2.42 (s, 3H), 2.29 (s, 6H), 2.25 (s, 6H), 2.24 (s, 6H) |

TABLE 1-continued

| Compound | Synthesis Method | Structure | $^1$H NMR (500 MHz, CDCl3, ppm) |
|---|---|---|---|
| 1,2-phenylene di(2,4,6-trimethylbenzoate) | D | 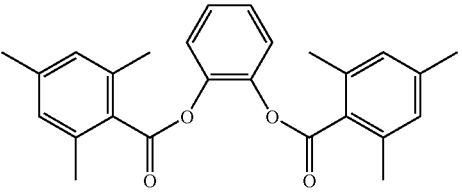 | δ 7.43 (m, 2H), 7.35 (m, 2H), 6.84 (s, 4H), 2.29 (s, 6H), 2.25 (s, 12H). |

It is specifically intended that the present disclosure not be limited to the embodiments and illustrations contained herein, but include modified forms of those embodiments including portions of the embodiments and combinations of elements of different embodiments as come within the scope of the following claims.

The invention claimed is:

1. A substituted phenylene aromatic diester of the structure (II):

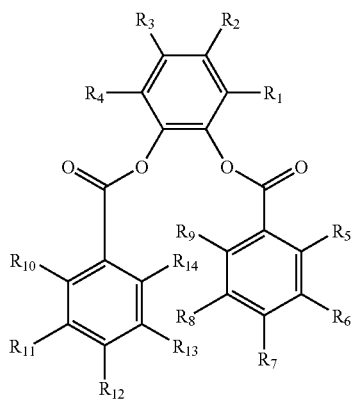

wherein $R_1$-$R_{14}$ are the same or different, $R_1$ is not an isopropyl group or a tertiary alkyl group, and each of $R_1$ and $R_3$ is selected from the group consisting of an unsubstituted alkyl group having 1 to 20 carbon atoms, an unsubstituted alkenyl group having 1 to 20 carbon atoms, a halohydrocarbyl group, a halogen, a silicon-containing hydrocarbyl group, and combinations thereof; and each of $R_2$, $R_4$, and $R_5$-$R_{14}$ is selected from the group consisting of hydrogen, an unsubstituted hydrocarbyl group having 1 to 20 carbon atoms, a halohydrocarbyl group, a halogen, and combinations thereof; and at least one of $R_5$-$R_{14}$ is a $C_1$-$C_8$ alkyl group or a halogen.

2. The substituted phenylene aromatic diester of claim 1 wherein each of $R_2$ and $R_4$ is hydrogen.

3. The substituted phenylene aromatic diester of claim 1 wherein $R_1$ is a methyl group and $R_3$ is a branched alkyl group.

4. The substituted phenylene aromatic diester of claim 1 wherein each of $R_1$ is a methyl group and $R_3$ is a t-butyl group.

5. The substituted phenylene aromatic diester of claim 1 wherein $R_1$ a methly group, $R_3$ is a t-butyl group and each of $R_7$ and $R_{12}$ is selected from the group consisting of a methyl group, an ethyl group, a fluorine atom, a chlorine atom, a bromine atom, and an iodine atom.

6. A substituted phenylene aromatic diester of claim 4 wherein $R_7$ is the same as $R_{12}$.

* * * * *